(12) United States Patent
Shen et al.

(10) Patent No.: US 12,221,617 B2
(45) Date of Patent: Feb. 11, 2025

(54) SCRaMbLE OF HETEROZYGOUS DIPLOID YEAST

(71) Applicant: New York University, New York, NY (US)

(72) Inventors: Michael Shen, New York, NY (US); Jef D. Boeke, New York, NY (US); Yi Wu, Tianjin (CN)

(73) Assignee: New York University, New York, NY (US)

( * ) Notice: Subject to any disclaimer, the term of this patent is extended or adjusted under 35 U.S.C. 154(b) by 1269 days.

(21) Appl. No.: 16/315,846

(22) PCT Filed: Jul. 7, 2017

(86) PCT No.: PCT/US2017/041194
§ 371 (c)(1),
(2) Date: Jan. 7, 2019

(87) PCT Pub. No.: WO2018/009863
PCT Pub. Date: Jan. 11, 2018

(65) Prior Publication Data
US 2019/0300910 A1    Oct. 3, 2019

Related U.S. Application Data

(60) Provisional application No. 62/359,403, filed on Jul. 7, 2016.

(51) Int. Cl.
| | | |
|---|---|---|
| C12N 15/90 | (2006.01) | |
| C12N 1/18 | (2006.01) | |
| C12N 3/00 | (2006.01) | |
| C12N 15/10 | (2006.01) | |
| C12N 15/52 | (2006.01) | |
| C12N 15/81 | (2006.01) | |

(52) U.S. Cl.
CPC ............. *C12N 15/905* (2013.01); *C12N 1/18* (2013.01); *C12N 3/00* (2013.01); *C12N 15/102* (2013.01); *C12N 15/52* (2013.01); *C12N 15/81* (2013.01); *C12N 2800/30* (2013.01)

(58) Field of Classification Search
CPC .......... C12N 15/905; C12N 1/18; C12N 3/00; C12N 15/102; C12N 15/52; C12N 15/81; C12N 2800/30
See application file for complete search history.

(56) References Cited

U.S. PATENT DOCUMENTS

| | | |
|---|---|---|
| 6,379,964 B1 | 4/2002 | Del Cardayre et al. |
| 2005/0120395 A1 | 6/2005 | Burt |
| 2015/0010984 A1 | 1/2015 | Bhalla et al. |
| 2016/0046972 A1 | 2/2016 | Boeke et al. |

FOREIGN PATENT DOCUMENTS

WO    2016/022363 A2    2/2016

OTHER PUBLICATIONS

Dejana Jovicevic, Developing a Synthetic Yeast for the Expression of Heterologous Genes using SCRAMbLE, Mar. 11, 2016, Imperial College London (Year: 2016).*
Elizabeth Louise Izolde Wightman, Exploring the Genome Rearrangement System, SCRaMbLE, to Introduce DNA into *Saccharomyces cerevisiae*, Oct. 9, 2015, Macquarie University (Year: 2015).*
Dejana Jovicevic, Developing a Synthetic Yeast for the Expression of Heterologous Genes using SCRAMbLE, Mar. 11, 2016, Imperial College London (Year: 2016) (Year: 2016).*
Jovicevic, Dejana. "Developing a Synthetic Yeast for the Expression of Heterologous Genes Using Scramble." Spiral, Oct. 2016 [retrieved on Jun. 5, 2023]. Retrieved from the Internet: <URL: spiral.imperial.ac.uk/handle/10044/1/60854 > (Year: 2016).*
Elizabeth Louise Izolde Wightman, Exploring the Genome Rearrangement System, SCRaMbLE, to Introduce DNA into *Saccharomyces cerevisiae*, Oct. 9, 2015, Macquarie University (Year: 2015) (Year: 2015).*
Craig (Molecular and cellular biology 5.12 (1985): 3517-3524) (Year: 1985).*
Scherthan (The Journal of cell biology 127.2 (1994): 273-285) (Year: 1994).*

(Continued)

*Primary Examiner* — Nancy J Leith
*Assistant Examiner* — Kyle T Rega
(74) *Attorney, Agent, or Firm* — Hodgson Russ LLP

(57) ABSTRACT

Provided are compositions and methods for making a diploid yeast having heterozygosity for at least one chromosome. The method includes mating haploid yeast having at least a first modified chromosome comprising a synthetic chromosome suitable for recombination-site-mediated evolution (as a SCRaMbLE-ready modification). The SCRaMbLE-ready modification includes introduced site-specific recombinase recognition sites that can be recognized by a recombinase. Yeast that have at least one SCRaMbLE-ready modification of a chromosome are mated with a haploid yeast devoid of the SCRaMbLE-ready modification to obtain diploid SCRaMbLE-ready yeast. Subsequent to mating the haploid SCRaMbLE-ready yeast to yeast devoid of the SCRaMbLE-ready modification the method includes using the recombinase to recombine the first modified chromosome to obtain heterozygous diploid yeast comprising at least one recombined (SCRaMbLEd) chromosome and a homologous non-SCRaMbLEd chromosome. The method further includes identifying heterozygous diploid yeast that comprise the at least one SCRaMbLEd chromosome that have a changed phenotype that is different from the phenotype of the diploid SCRaMbLE-ready yeast. Yeast made by the methods, compositions of matter made by the yeast, spores made by the yeast, and kits containing the yeast and/or their spores are included.

15 Claims, 11 Drawing Sheets

(56) References Cited

OTHER PUBLICATIONS

Dymond, J.S., et al., Synthetic chromosome arms function in yeast and generate phenotypic diversity by design, Nature, Sep. 22, 2011, vol. 477, pp. 471-476.
David, F. and Siewers, V., Advances in yeast genome engineering, FEMS Yeast Research, Feb. 1, 2015, vol. 15, pp. 1-14.
Greig, D., et al., Hybrid Speciation in Experimental Populations of Yeast, Science, Nov. 29, 2002, vol. 298, pp. 1773-1775.
Dymond, J.S. and Boeke, J., The *Saccharomyces cerevisiae* SCRaMbLE system and Genome Minimization, Bioengineered Bugs, May 1, 2012, vol. 3, No. 3, pp. 170-173.

* cited by examiner

C

| strain | location | structure variation | SCRaMbLEd segments | ORFs | size (bp) | |
|---|---|---|---|---|---|---|
| yYW166 | A | deletion | 2-9 | YJL222W-YJL217W | 17031 | |
| | B | deletion | 40-61 | YJL161W-YJL130C | 58298 | |
| | C | deletion | 112-127 | YJL052C-YJL028W | 51548 | blue |
| | D | duplication | 128-131 | YJL027C-YJL022W | 6544 | |
| | E | deletion | 166 | none | 810 | |
| | F | deletion | 194-248 | YJR093C-YJR159W | 137041 | |
| yYW167 | G | deletion | 47-53 | YJL154C-YJL140W | 20815 | |
| | H | deletion | 73 | none | 386 | red |
| | I | deletion | 173-174 | YJR055W-YJR056C | 3548 | |
| | J | deletion | 246-247 | none | 1047 | |

FIG. 2 (cont.)

SCRaMbLE OF HETEROZYGOUS DIPLOID YEAST

CROSS REFERENCE TO RELATED APPLICATIONS

This application claims priority to U.S. provisional application No. 62/359,403, filed Jul. 7, 2016, the disclosure of which is incorporated herein by reference.

STATEMENT REGARDING FEDERALLY SPONSORED RESEARCH

This invention was made with government support under grant number MCB-1026068, MCB-1158201, and MCB-1616111 awarded by the National Science Foundation. The government has certain rights in the invention.

FIELD OF THE DISCLOSURE

The disclosure generally relates to engineered yeast and more particularly to hybrid diploid yeast strains incorporating one or more synthetic chromosomes that are subject to controlled recombination.

BACKGROUND

The SCRaMbLE (Synthetic Chromosome Recombination and Modification by LoxP-Mediated Evolution) system, developed as part of the Sc2.0 project, allows for the inducible rearrangement of synthetic chromosomes by the Cre recombinase enzyme. The design of synthetic chromosomes[1] specifies encoding the palindromic 34 bp recombination site loxPsym[2] throughout the genome 3 bp downstream of the stop codon of all nonessential open reading frames (ORFs). Additional loxPsym sequences are inserted in place of deleted non-intronic features and a "thinning" algorithm ensures the minimum inter-loxPsym site distance is greater than 300 bp. Conventional loxP sites are directional, and the orientation of any pair of loxP sites relative to each other dictates whether a deletion, inversion, or translocation will occur. LoxPsym sites are nondirectional[2], enabling the stochastic generation of deletions, duplications, inversions, and/or translocations within and between synthetic chromosomes[4]. This SCRaMbLE system allows for exploration and characterization of a huge number of potential genomic rearrangements via expression of Cre-recombinase in the nucleus of synthetic chromosome-bearing cells. Controlling the activity of Cre is important for maintaining chromosome stability; to implement this, Cre is fused to the estrogen binding domain (EBD)[3], which effectively sequesters Cre in the cytosol. Only upon treatment with estradiol does Cre-EBD translocate into the nucleus and becomes available to recombine loxPsym sites. This system can generate strains with phenotypes that differ from their non-SCRaMbLEd parent.

However, the random nature of SCRaMbLE events can also lead to a number of sub-optimal outcomes with regards to studying rearrangements in an unbiased fashion. SCRaMbLE of haploid strains bearing one or more synthetic chromosomes results in a high lethality rate due to the deletion of one or more essential genes[4-5]. Additionally, deletion of important, but nonessential genes may mask an otherwise apparent improvement of phenotype. Finally, SCRaMbLE of synthetic chromosome bearing strains has thus far been done in a *S. cerevisiae* laboratory strain background, limiting its industrial applications. Thus, there is an ongoing need to improve SCRaMbLE, and to provide new and industrially useful diploid strains created using it. The present disclosure is pertinent to these needs.

SUMMARY OF THE DISCLOSURE

The present disclosure relates to improved approached to using SCRaMbLE, which is a genome restructuring technique that can be used in synthetic genomes such as that of Sc2.0, the synthetic yeast genome, which contains hundreds to thousands of strategically positioned loxPsym sites. SCRaMbLE has been used to induce genome rearrangements in either yeast strains harboring one or more synthetic chromosomes or of plasmid DNA in vitro and in vivo. The present disclosure provides compositions and methods for creating engineered heterozygous diploid strains that contain a modified chromosome homolog and a wild type homolog for each yeast chromosome. The disclosure provides a collection of heterozygous diploid strains derived by mating a haploid semisynthetic and a haploid native parental strain. It is demonstrated that such heterozygous diploid strains are more robust to SCRaMbLE than haploid strains, that SCRaMbLE of heterozygous diploids can result in rapid improvement of rationally selected phenotypes, and established that multiple sets of independent genomic rearrangements are able to lead to similar phenotype enhancements.

In certain embodiments the disclosure provides a method for making a diploid yeast having heterozygosity for at least one chromosome, the method comprising: i) mating haploid yeast having at least a first modified chromosome comprising a synthetic chromosome suitable for recombination-site-mediated evolution (referred to herein as a SCRaMbLE-ready modification) wherein the SCRaMbLE-ready modification comprises introduced site-specific recombinase recognition sites that can be recognized by a recombinase. The disclosure includes SCRaMbLE-ready haploid yeast that have never previously been exposed to the recombinase that recognizes the recombinase recognition site. Likewise, the disclosure includes the SCRaMbLE-ready diploid yeast prior to the recombination that is produced via the recombinase activity of the recombinase that recognizes the introduced recombinase recognition sites. The disclosure includes yeast wherein the recombinase recognition sites that are introduced into the SCRaMbLE-ready chromosomes are the only such recombinase recognition sites in the yeast genome.

Yeast comprising at least one SCRaMbLE-ready modification of a chromosome are mated with a haploid yeast devoid of the SCRaMbLE-ready modification to obtain diploid SCRaMbLE-ready yeast. Subsequent to mating the haploid SCRaMbLE-ready yeast to yeast devoid of the SCRaMbLE-ready modification (i.e., mating with wild type haploid yeast) the method includes using the recombinase to recombine the first modified chromosome to obtain heterozygous diploid yeast comprising at least one recombined (SCRaMbLEd) chromosome and a homologous non-SCRaMbLEd chromosome. The method further includes identifying heterozygous diploid yeast that comprise the at least one SCRaMbLEd chromosome that have a changed phenotype that is different from the phenotype of the diploid SCRaMbLE-ready yeast. Thus, diploid SCRaMbLE-ready yeast can be used as a control for any parameter and/or phenotype. In embodiments, the disclosure includes selecting heterozygous diploid yeast that comprise at least one SCRaMbLEd chromosome by comparing any parameter and/or phenotype of the heterozygous diploid yeast that comprise at least one SCRaMbLEd chromosome to any suitable control, which can be any value or other reference that is, for example, obtained by observing, measuring, and/or quantifying diploid SCRaMbLE-ready yeast. In embodiments, a changed phenotype that can be used to identify and/or select heterozygous diploid yeast that comprise at least one SCRaMbLEd chromosome includes but is not limited to a change in growth rate, growth at a temperature at which the SCRaMbLE-ready yeast do not grow, resistance to a chemical compound, production of a product that is not produced by the diploid SCRaMbLE-ready yeast, production of more of a product than is produced by the diploid SCRaMbLE-ready yeast, or a combination thereof. The products can include any product, such as a protein, which may or may not be an enzyme, metabolic products produced by the proteins, and any other product that can be produced by yeast.

In certain and non-limiting approaches the disclosure includes using the recombinase by inducing expression of the recombinase, such as from an inducible promoter, and/or inducing translocation of the recombinase into the nucleus of the diploid SCRaMbLE-ready yeast, such that at least the first modified chromosome is recombined. In embodiments, heterozygous diploid yeast that have the changed phenotype are subjected to a selection pressure prior to selection, and are then identified based at least in part on a the changed phenotype that is correlated with being subjected to the selection pressure. In embodiment, the selection pressure comprises exposure to an antibiotic, or to a non-antibiotic small drug molecule, or a change in culture media component, or a change in temperature, or a combination thereof. In certain embodiments the selection pressure comprises an increased temperature in which the heterozygous diploid yeast are grown. The increased temperature includes, but is not limited to a temperature of between 38 and 42 degrees Celsius, inclusive, and wherein the change in the heterozygous diploid yeast that is correlated with the increased temperature comprises survival. In embodiments, the using the recombinase to cause recombination of the SCRaMbLE-ready chromosome is performed for not more than from 6 hours, up to 24 hours, but longer times can be used, such as for a period of days.

In embodiments, heterozygous diploid yeast of this disclosure are *S. cerevisiae* or *S. paradoxus*. In embodiments, haploid yeast having the SCRaMbLE-ready modification are *S. cerevisiae* or *S. paradoxus*. In embodiment, the haploid yeast devoid of the SCRaMbLE-ready modification are the other of the *S. cerevisiae* or *S. paradoxus* that the haploid yeast having the SCRaMbLE-ready modification are not.

In embodiments, the recombinase recognition sites of comprises a loxP site or a derivative thereof. The derivative may be loxPsym sites. In certain implementations the recombinase recognition site is duplicated in a first modified chromosome, and as such the first modified chromosome thus comprises at least two of the recombinase recognition sites. In embodiments, the recombinase that recognizes the recombinase recognition site is Cre recombinase or a modified Cre recombinase. In embodiment, the modified Cre recombinase comprises a Cre-estrogen binding domain.

In embodiments the disclosure includes a heterozygous diploid yeast clonal population made according any method described herein. Such yeast clonal populations can be preserved using any suitable approach and/or reagent(s), and includes but is not limited to heterozygous diploid yeast populations that are preserved at a refrigerated or a freezing temperature or are dried or are freeze dried. The disclosure includes mixed populations of heterozygous diploid yeast comprising distinct SCRaMbLEd chromosomes.

In another aspect the disclosure provides a kit comprising heterozygous diploid made according to any method described herein, and the kit may further include at least one container holding the yeast. The kit can optionally include instructions for growing and/or using the yeast.

The disclosure includes any composition of matter made by modified yeasts described herein, and such compositions of matter can be isolated from the culture medium in which the yeast are grown, and such compositions of matter may be purified to any desired degree of purity. The culture medium itself is also included in the invention. The disclosure also includes spores produced by a modified yeasts described herein. Such spores may also be included in kits of this disclosure, and may be substituted for the yeast in the kits.

(c) The POL32 gene with 500 bp upstream/300 bp downstream sequence was cloned from BY4741 into the episomal plasmid pRS416 and the resulting plasmid pRS416-POL32 transformed into yMS521. These strains were compared via serial dilution assay to the SCRaMbLEd strain yYW185 transformed with pRS416, yMS521 transformed with pRS416, or BY4743 transformed with pRS416 on SC-Ura+4 mg/mL caffeine.

Figure 4:
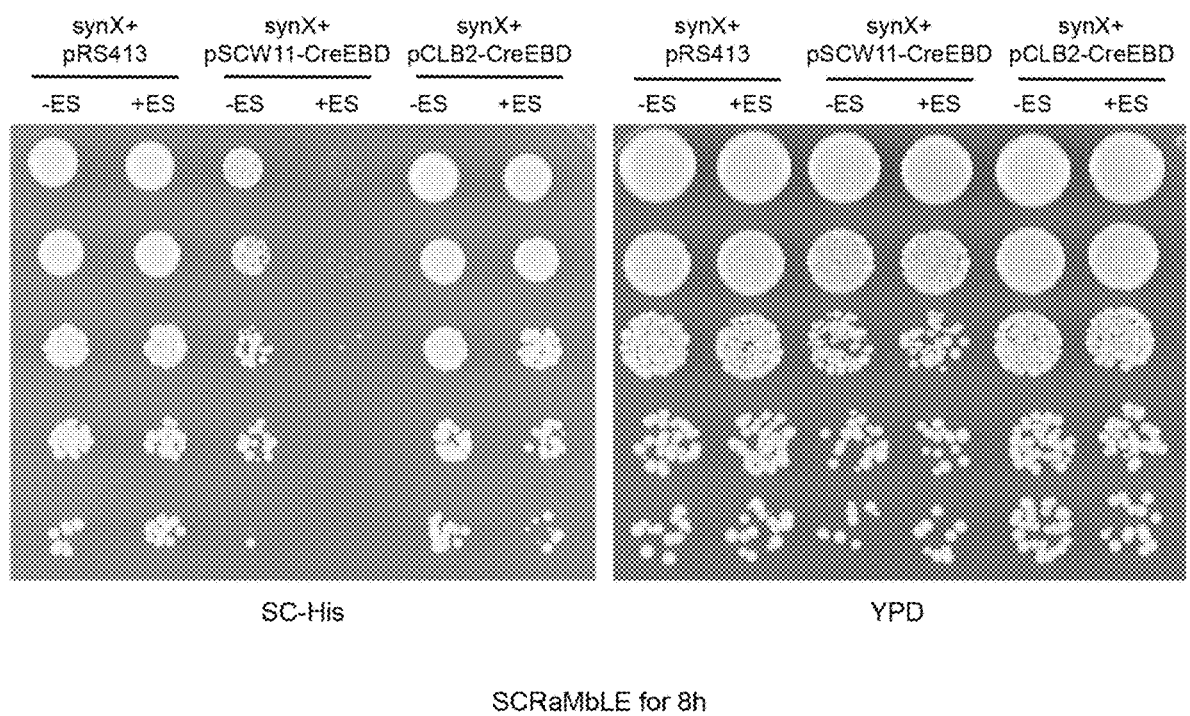

FIG. 4: Comparison of pSCW11 and pCLB2 promoters for Cre-EBD. Strains bearing synX were transformed with the episomal shuttle vector pRS413 or pRS413 expressing Cre-EBD driven by either pSCW11 or pCLB2. Strains were subjected to SCRaMbLE for 8 hours in SC-His media without estradiol (−ES) or SC-His media with 1 μM β-estradiol (+ES) and were subsequently washed and plated as a serial dilution assay onto SC-His or YPD plates.

Figure 5:
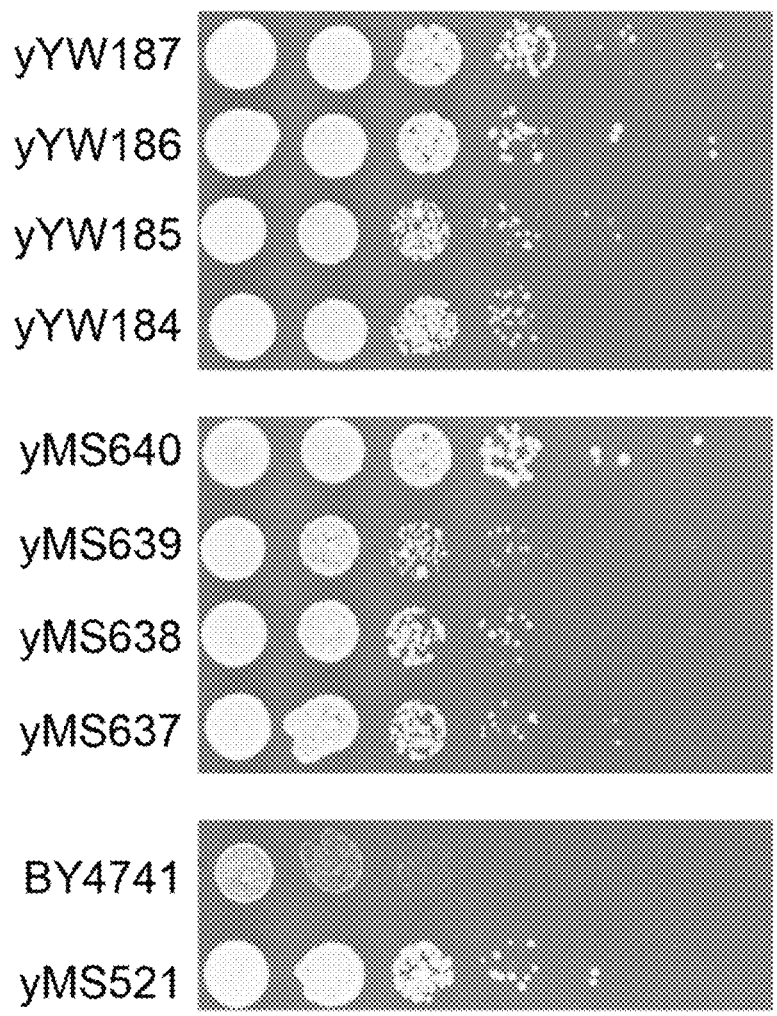

FIG. 5: Growth of SCRaMbLEd, caffeine-tolerant CBS5829-synX and CBS5829-synVsynX strains in rapamycin. A serial dilution assay on YPD containing 2 μg/mL rapamycin was used to compare the non-SCRaMbLEd CBS5829-synX parent strain yMS521 with 8 SCRaMbLEd strains (yMS637-640, yYW184-187), all of which show an increased tolerance for caffeine compared to yMS521.

Figure 6:
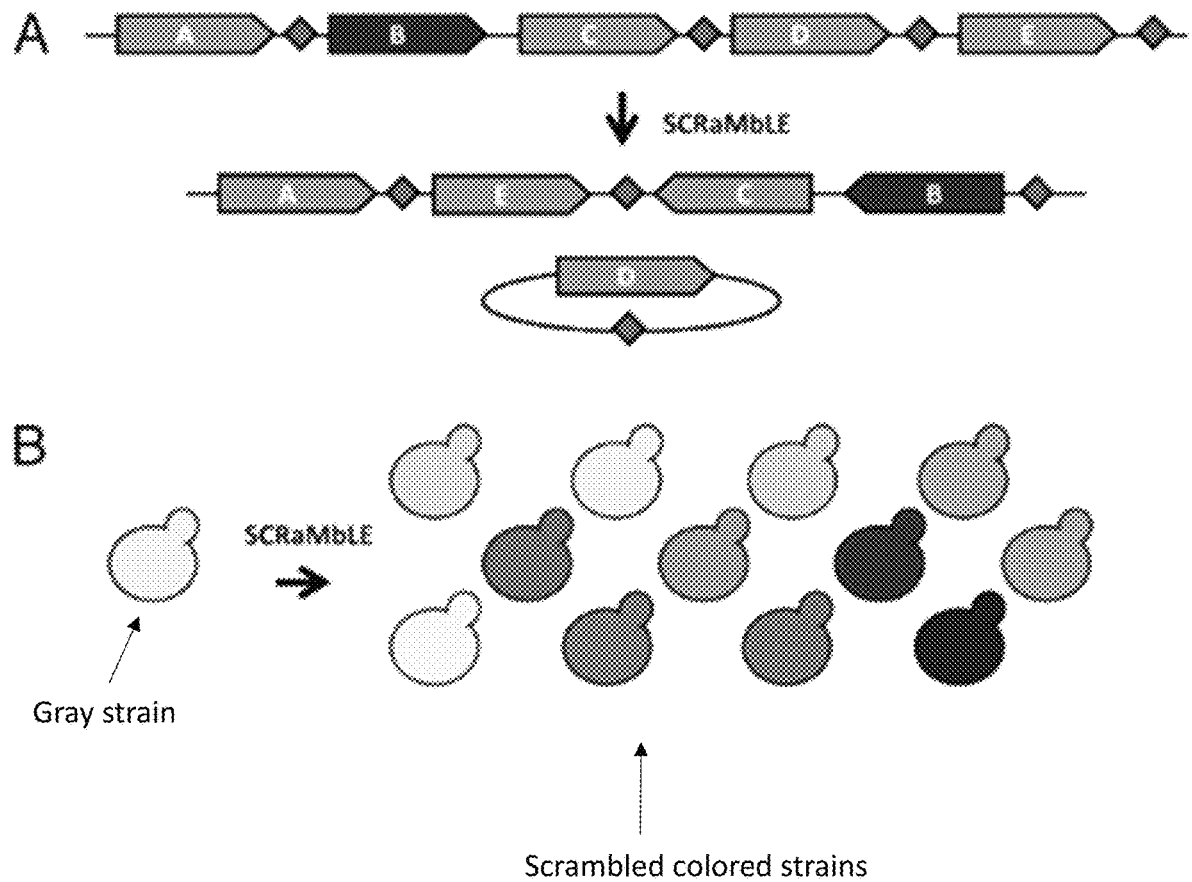

FIG. 6: Schematic depicting how SCRaMbLE restructures a yeast genome. (A) LoxPsym sites (diamonds) are inserted in the 3'UTR of non-essential genes (arrows A, C, D, and E); essential genes (arrow B) do not have an associated loxPsym site. The symmetry of loxPsym sites permits both translocations/inversions and deletions at each site. Complex rearrangements result from induction of SCRaMbLE. In the example shown, genes "B" and "C" are inverted, "E" has been excised and reintegrated, and "D" has been lost from the SCRaMbLEd chromosome. (B) Induction of SCRaMbLE in a synthetic strain (gray) results in a significant increase in genetic diversity (colors). Following selection for a desired phenotype, which can range from simple viability to increased ability to produce a desirable substance, genome content and structure of SCRaMbLEd strains can be analyzed by PCRTag analysis, comparative genome hybridization (CGH), molecular karyotyping and/or whole-genome sequencing.

DESCRIPTION OF THE INVENTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all steps and compositions of matter described herein in the text and figures of this disclosure, including all such steps individually and in all combinations thereof, and includes all compositions of matter including but not necessarily limited to vectors, cloning intermediates, cells, cell cultures, etc. All individual yeast strains described herein are included in the invention.

This disclosure provides a method to construct hybrid diploid yeast strains incorporating synthetic chromosomes constructed as part of the Sc2.0 or the synthetic yeast genome project. Thus, in certain embodiments the disclosure provides "designer" yeast genomes based on *Saccharomyces cerevisiae*. The resulting Sc2.0 strains may be fully or partially synthetic (i.e. contain one or multiple synthetic chromosomes on a background of native chromosomes). An aspect of this system is referred to as SCRaMbLE which involves the introduction of symmetric loxP (loxPsym) recombination sites at specific points in each artificial chromosome, and allows for random deletion, inversion, duplication, and/or translocation of the DNA segments in between loxPsym sites when the cell expresses the Cre recombinase enzyme.

An aspect of this invention stems from the use of SCRaMbLE genome evolution in a heterozygous diploid. This confers important advantages over the previously described SCRaMbLE of haploid yeast strains, such as described in Shen Y, Stracquadanio G, Wang Y, et al. SCRaMbLE generates designed combinatorial stochastic diversity in synthetic chromosomes. *Genome Research*. 2016; 26(1):36-49. doi:10.1101/gr.193433.115, and Dymond J, Boeke J. 2012. The *Saccharomyces cerevisiae* SCRaMbLE system and genome minimization. Bioeng Bugs 3: 168-171, and Dymond J S, Richardson S M, Coombes C E, et al. Synthetic chromosome arms function in yeast and generate phenotypic diversity by design. *Nature*. 011; 477(7365):471-476. doi:10.1038/nature10403. The descriptions of the SCRaMbLE method and modified yeasts produced by the methods from each of these references are incorporated herein by reference. The first advantage is shown through decreased lethality. During SCRaMbLE of a haploid organism bearing one or more synthetic chromosomes, deletion of an essential gene by loxP-mediated recombination invariably proves fatal to the cell in which this event occurred. However, in the heterozygous diploids we constructed, only one copy (out of two) of any essential gene can be removed via SCRaMbLE (the copy from the native parent would not be flanked by loxPsym sites). With one remaining copy of an essential gene, there is a chance that the strain is still viable, leading to the ability to generate a larger, more diverse population of genomic architectures.

An aspect of this disclosure includes improving the performance of industrial strains through "gain of function" obtained when one or more genes is duplicated through SCRaMBLe. However, a downside of the method as originally described in haploid strains, is that genes can be lost by deletion as well as gained through duplication. Thus many potentially valuable strains may be lost through deletion of essential genes, or have their performance diminished as a consequence of deletion of important genes. Accordingly, the current disclosure provides a major improvement in the performance of SCRaMbLE, which is based on maintaining a second, non-SCRaMBLe-sensitive copy of the genome to be SCRaMbLed in the same strain, i.e., a heterozygous diploid strain is used rather than a haploid. One set of genes is in a "native" state lacking loxPsym sites, and the other set of genes is flanked by loxPsym sites and is thus "SCRaMbLE-ready".

Further, we show that we are able to use the SCRaMbLE inducible genomic rearrangement system built into synthetic chromosomes to increase the genetic diversity of heterozygous diploids derived from a single synthetic or semisynthetic parental engineered strain. That is, a single strain can be mated to a diverse panel of wild, industrial or brewing strains, generating an arbitrarily large panel of strains with diverse natural properties that greatly augments the applications of SCRaMbLE. We show that this increased genetic diversity can be used to select for SCRaMbLEd cells that have especially robust phenotypes in particular conditions (extreme temperature tolerance, tolerance to caffeine) that are not observed in non-SCRaMbLEd cells. Thus, in various embodiments the disclosure comprises identifying heterozygous diploid yeasts that have been subjected to recombination by a recombinase by identifying a difference in the recombined yeast, relative to the non-recombined diploid yeast, i.e., yeast that are SCRaMbLE-ready, but prior to recombination.

This disclosure accordingly provides at least two aspects. 1) The construction of heterozygous diploid strains of *S. cerevisiae* from one wild-type haploid "parent" and one Sc2.0 "parent" bearing one or more synthetic chromosomes, or even just a segment of a synthetic chromosome, which are referred to herein as semi-synthetic. The term semi-synthetic thus refers to a strain that has more than one synthetic chromosome, and includes strains that comprise only a part of a synthetic chromosome. 2) The use of SCRaMbLE to generate super-optimal phenotypes from such heterozygous diploid strains.

As described above, the SCRaMbLE technique only as applied to haploid strains is known in the art. FIG. 6 provides a schematic illustrating the SCRaMbLE approach. Thus, haploid strains subjected to SCRaMbLE as referred to herein comprise, for example, sets of introduced recombinase recognition sites, such as LoxPSym sites, wherein the recombinase recognition sites flank one or more non-essential genes, and wherein essential genes are not flanked by LoxPSym sites. Thus, heterozygous diploid yeast strains that have been subjected to SCRaMbLE (i.e., have been recombined using a recombinase as described herein) can include a variety of genetic rearrangements, including but not necessarily limited to removal of certain genetic elements, such as Retrotransposons, Subtelomeric repeats, and Introns, as well as inversions, repeated chromosomal segments, deletions of chromosomal segments, and chromosome rearrangements.

In more detail, the heterozygous diploids of this disclosure are derived from the joining of a haploid semisynthetic or synthetic and a haploid native parental genome. The semisynthetic or synthetic parental genome may include one or more synthetic chromosomes synthesized as part of the Sc2.0 project and bearing loxPsym sites that allow for recognition by Cre recombinase (or an alternative recombinase) or may comprise newly generated haploid cells with newly developed modified chromosomes as further described herein, including but not necessarily limited to diploid heterozygous cells that comprise a SCRaMbLE-ready chromosome that is capable of being modified by the action of recombinase which is not necessarily limited to Cre or to loxPsym or loxP sites. In this regard, the disclosure comprises use of other recombinase recognition sequences and site specific recombinases that recognize such sequences, but it is preferable and in certain embodiments required for the recombinase recognition sequences to be unique to the modified chromosome, i.e., they do not appear elsewhere in yeast genome, except as otherwise described herein. In certain approaches the disclosure comprises use of recombinase systems which may include but are not necessarily limited to Flp Recombinase which functions in the Flp/FRT system, the Dre recombinase which functions in the Dre-rox system, the Vika recombinase which functions in the Vika/vox system, Bxb1 recombinase which functions with attP and attB sites, long terminal repeat (LTR) site-specific recombinase (Tre), and other serine recombinases, such as phiC31 integrase which mediates recombination between two 34 base pair sequences termed attachment sites (att), Hin recombinase, which recognizes 26 bp imperfect inverted repeat sequences or int2-13 each of which each recognizes distinct target sites of 39-66 bp. Further, the recombinase may be modified, and/or its expression and/or function may be contingent upon for example, the presence of a small molecule or a compound. In certain embodiments expression of the recombinase may be dependent upon, for example, estradiol, IPTG (isopropyl thioglactoside), virginiamycin, gentamycin, quercetin, lincomycin, 1-Naphthaleneacetic acid, 2,4-DAPG, 3-oxo-octanoyl-L-homoserine (OAH), bepridil, catechin, choline, coumestrol, cumate, d-camphor, daidzein, doxycycline, erythromycin, fisetin, fusaric acid, genistein, kinetin, or sodium salicylate. Such agents may, for example, be required to initiate transcription of the mRNA encoding the recombinase by inducing transcription from a promoter that drives transcription of the mRNA. In certain embodiments the disclosure includes use of a modified recombinase. In one embodiment the disclosure relates to use of a CRE gene fused to the estrogen binding domain (EBD) of an estrogen receptor, and/or use of a Cre-EBD chimeric protein otherwise expressed and/or present in the cell for at least a period of time sufficient to facilitate modification of the chromosome comprising Cre-recognition sites.

The native parental genome can be derived from a wide variety of natural *Saccharomyces cerevisiae* strains, including ones used in industrial processes such as winemaking, beer brewing, nutrition, and environmental modulation. We have also demonstrated that heterozygous diploids can be made with a native parental genome from *Saccharomyces paradoxus*, the closest known relative to *S. cerevisiae*, which indicates that this technique could be expanded to other interfertile yeast species.

In non-limiting demonstrations the disclosure involves thermotolerance, which is a particularly useful trait for industrial yeast strains used in processes such as biofuel production and fermentation. *Saccharomyces cerevisiae* can respond to heat stress in a number of ways, including adopting transient aneuploidy and altering sterol composition. However, traditional evolution of stress-tolerant yeast strains can take on the order of hundreds or thousands of generations, whether performed in haploid or diploid strains. The present disclosure solves this problem by providing efficient recombination using short periods of time during which induction of the expression of the recombinase is performed.

While certain embodiments of this disclosure are illustrated using heterozygous diploid yeast, this scrambles only the "synthetic" set of genes and not the "native" set of genes that derive from the wild parent. However, given the benefit of the present disclosure, it will be apparent to those skilled in the art that it is possible to scramble the native strain as well, as follows. Once the heterozygous diploid is built, and in the absence of a recombinase, and/or a recombinase that is translocated to the nucleus, including but not limited to a recombinase produced from, for example, a Cre-EBD plasmid), it is possible to make a very large collection of meiotic haploid derivatives of the parental diploid strain. The genome of each such random spore will contain 50% derived from the "synthetic or semisynthetic parental genome, and 50% from the "native" parental genome. This is due to extensive meiotic recombination which will occur genome wide. The recombination break-points will place loxPsym sites or alternatives of such sites adjacent to native DNA. Very large collections of such spores can be isolated by a variety of methods well known in the art. These collections could then be back-crossed en masse to either the native or synthetic/semisynthetic parent. Within this collection, every genomic region in the native strain will be represented in a fragment flanked by loxP sites. Thus the native parental genome will also be subject to scrambling.

It will be recognized that the present disclosure provides methods to generate synthetic or semi-synthetic heterozygous diploid yeast strains. These strains have included dozens of parents coming from collections of either S. cerevisiae or S. paradoxus strains, indicating this method could likely be extended to other yeast species. Importantly, this finding enables the creation of heterozygous diploid strains that combine properties of their wild-type parents and the genetic flexibility of their synthetic chromosome bearing parents, allowing the generation of quantitative phenotypes of greater magnitude than the original parent strains are able to display. In a non-limiting embodiment, this phenotype enhancement is achieved through one SCRaMbLE process, which is considerably less time than traditional evolution approaches. In embodiments, the period during which recombination is permitted is not more than 24 hours, or is not more than 12 hours, or is not more than 6 hours. It will be recognized that this process can repeated multiple times until any particular phenotype is identified, such phenotypes including but not limited to optimized properties in connection with any particular parameter described herein.

The disclosure includes but is not limited to the generation of new strains of yeast particularly well suited for growth in extreme conditions (heat, pH, non-glucose carbon sources) for use in fermentation, biofuel production, and other industrial processes. Each industrial strain can be mated to a synthetic strain and the resultant diploid SCRaMbLEd and subsequently selected for a specific phenotype of interest.

It will be apparent from the Examples, figures and tables herein that this disclosure in this work, we have described a set of strains and methodology that address many drawbacks of the SCRaMbLE system. By inducing SCRaMbLE in heterozygous diploids which contain a "wild-type" counterpart to each synthetic chromosome, we reduce the frequency by which a deleterious SCRaMbLE event, i.e. deletion of an essential gene, is fatal to the cell in which it occurs. By creating a collection of such heterozygous diploids using both S. cerevisiae and S. paradoxus strains, we have shown that SCRaMbLE is a technique that can be successfully applied to a variety of hybrid strain backgrounds.

Additionally, SCRaMbLE of heterozygous diploids is able to rapidly generate desired phenotypes in a well-controlled fashion. The pCLB2-Cre-EBD construct we employ for SCRaMbLE displays less background activity than pSCW11-Cre-EBD used in previous work and allows for robust induction of SCRaMbLE by β-estradiol in a single, 6-hour experiment, or other time frames as described herein.

As will be recognized by those skilled in the art, the importance of yeast as a domesticated microbe has been evident for thousands of years, beginning with its importance in the production of food and beverage. Due to the broad range of environmental conditions these microbes must endure, generation of strains with higher tolerance for temperature, pH, etc. for industrial applications is an important goal for biotechnology. In this disclosure we demonstrate the rapid improvement of thermotolerance in a Y12-synXheterozygous diploid as one such example which may have applications for the brewing industry due to the use of the Y12 strain as a sake yeast. That we are able to generate a significant increase in thermotolerance during a short, relatively weak pulse of SCRaMbLE activity in a strain harboring only one synthetic chromosome indicates further optimization of this phenotype using iterative cycles of SCRaMbLE and incorporation of additional synthetic chromosomes can be performed, and this approach can be adapted for other strains made according to the compositions and methods described herein.

Embodiments of this disclosure also demonstrate the power of SCRaMbLE in heterozygous diploids for discovery of novel biological function. For example, using the CBS5829-synX hybrid strain, we demonstrate improvement in caffeine tolerance that, in two of the presently disclosed SCRaMbLEd strains, can be at least partially attributed to an increase in copy number of the POL32 gene, one previously unlinked to caffeine resistance. We originally hypothesized that our sequencing would reveal an increase in copy number of TOR1, the kinase subunit of the TORC1 complex which caffeine has been shown to inhibit in budding yeast[14]. While we did not observe this in 10 sequenced strains, we were able to recapitulate a modest increase in caffeine tolerance by addition of an episomal copy of POL32 to our non-SCRaMbLEd parent Y12-synX strain. Thus, multiple stochastic, unlinked, SCRaMbLE events can result in the expression of one particular phenotype. Copy number analysis of multiple strains displaying the same phenotype can be analyzed to determine additional biological frameworks.

We found a number of inversions present in SCRaMbLEd strains with increased tolerance of environmental or chemical stresses (table 3), testing the effect of individual inversions on phenotype is more challenging than evaluating the impact of deletions or duplications. Also, the stochasticity of SCRaMbLE can result in major disruptions of genome structure, as evidenced by the large deletions in synX of yYW166 and yYW167. Thus, verification of phenotype can accordingly be integrated into the heterozygous diploid SCRaMbLE workflow.

We have used two specific strains as illustrative examples of how SCRaMbLE in heterozygous diploids is able to generate both industrially relevant gains in phenotype and new biological knowledge. The immense diversity of yeasts, both domesticated and wild, as well as the completion of more synthetic chromosomes as part of the Sc2.0 project[6,7,16,17,18] is expected allow for a more top-down approach to achieve development of new strains, given the benefit of the current disclosure. Thus, by rationally choosing the "wild-type" strain and the synthetic chromosomes incorporated in a heterozygous diploid, the probability of generating a specific phenotypic outcome can be increased. Further expansion of the mating partner for synthetic chromosome bearing strains could be achieved using physical methods such as spheroplast fusion[19]. Thus, compositions and methods of the present disclosure are expected to enable the acceleration of biological discovery and productive industrial microbe evolution.

Figure 1:
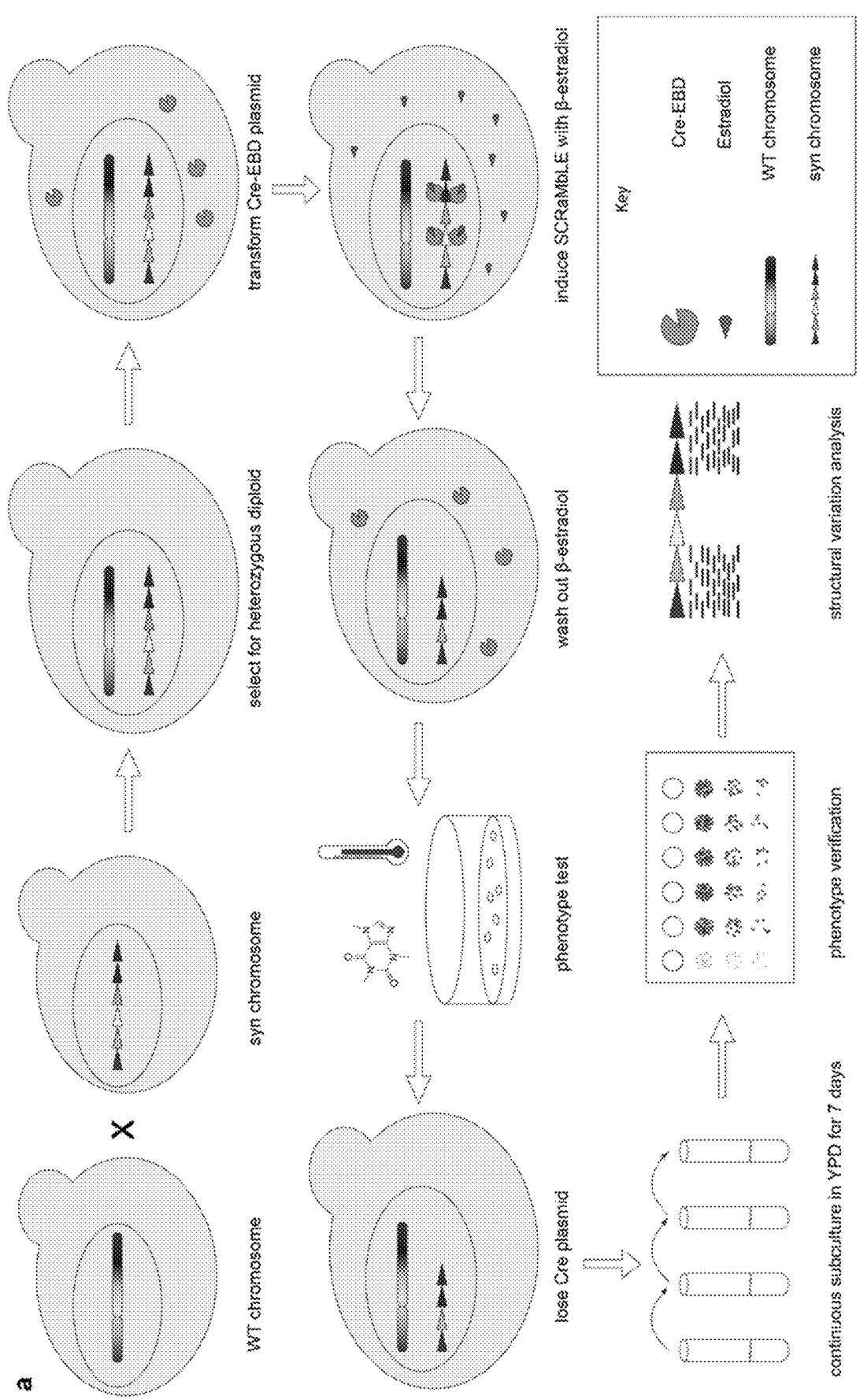
FIG. 1: Construction of a set of heterozygous diploid yeast strains containing one or more synthetic chromosomes. (a) Experimental workflow. A *S. cerevisiae* strain bearing one or more synthetic chromosomes is mated to a *S. cerevisiae* or *S. paradoxus* strain with a "wild-type" genome. The resultant heterozygous diploid cells can be selected for, SCRaMbLEd, and tested for tolerance of a variety of environmental and chemical conditions. Strains showing increased fitness have their phenotype verified and can be analyzed with whole genome sequencing to determine the sets of SCRaMbLE events responsible for a given phenotype. (b) SCRaMbLE of haploid and heterozygous diploid synVsynX yeast was induced by adding 1 µM β-estradiol to culture media for 6 h. Heterozygous diploid S288C-synVsynX strains demonstrate a lesser degree of SCRaMbLE-mediated lethality at both 30° C. and 37° C. compared to haploid synVsynX strains. (c) Heterozygous diploid strains incorporating a variety of *S. cerevisiae* "wild-type" genomes are robust to SCRaMbLE. Additionally, heterozygous diploid strains containing two synthetic chromosomes can be SCRaMbLEd without appreciable loss in viability compared to strains containing one synthetic chromosome.
Figure 1:
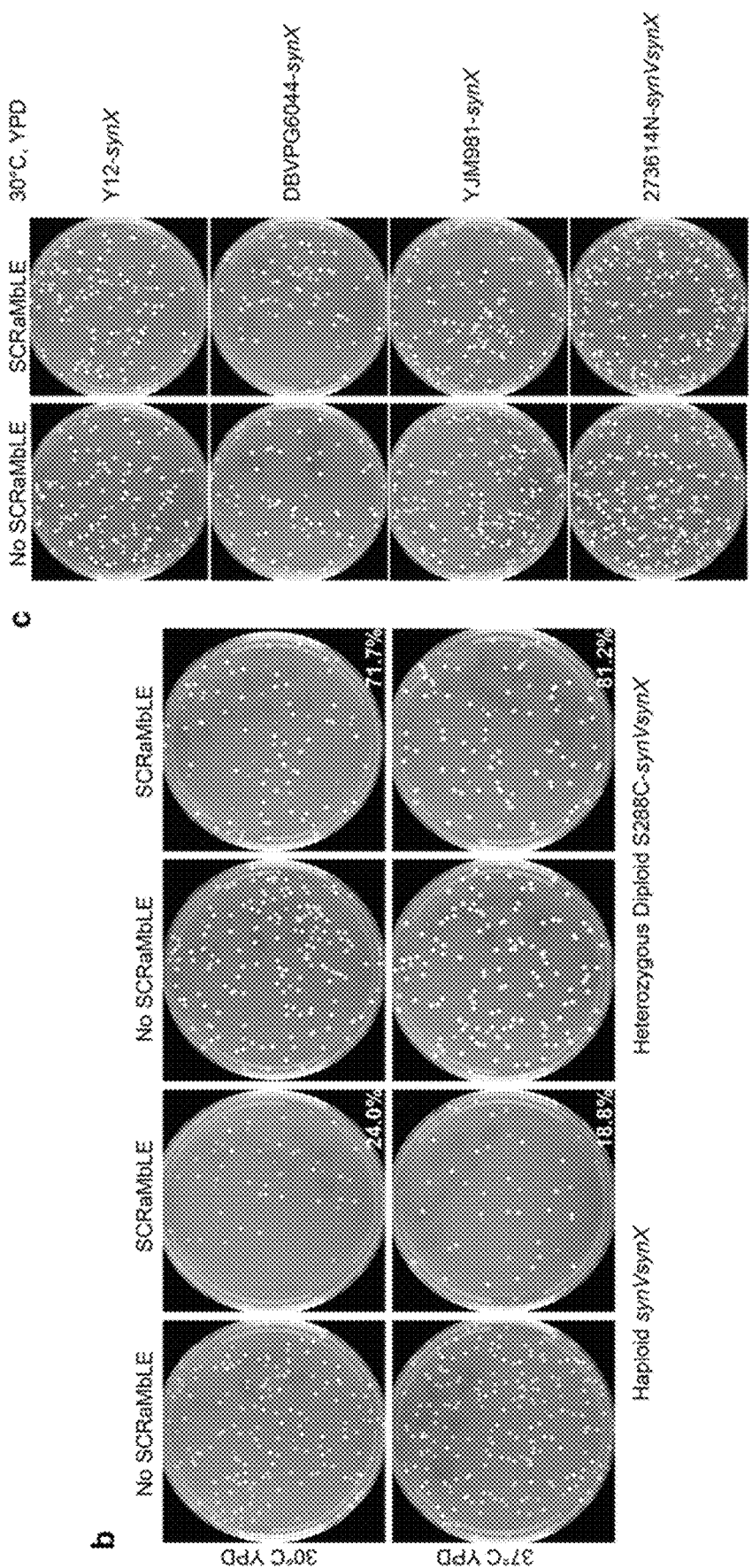

The following Examples are intended to illustrate but not limit the invention. Further, the Examples illustrate improvements of previous, haploid only implementations of SCRaMbLE via the construction of a set of heterozygous diploid yeast strains. Each member of this collection is constructed by the mating of a haploid strain bearing either one (chromosome X) or two (chromosomes V and X) synthetic chromosomes,[6-7] with a haploid strain from the Saccharomyces Genome Resequencing Project (SGRP) strain set[8-9]. Synthetic chromosome X (synX) was designed as 707,459 base pairs and includes 245 loxPsym sites, while synthetic chromosome V (synV) was designed as 536,024 base pairs and includes 176 loxPsym sites. The SGRP set contains both S. cerevisiae and S. paradoxus haploids, both of which were successfully mated to synthetic chromosome bearing strains to generate two series of intraspecies diploids and interspecies diploids (FIG. 1a, Table 2).

Example 1

Upon generation and validation of the heterozygous diploid strains, we first demonstrated their increased tolerance to the effects of SCRaMbLE. Strains were transformed with an episomal, URA3-bearing plasmid encoding Cre-EBD (Cre recombinase fused to the Estrogen Binding domain) and SCRaMbLE was induced for 6 hours using 1 µM β-estradiol. We chose to use Cre-EBD driven by the CLB2 promoter, as we found this resulted in less leaky expression of Cre when compared to Cre-EBD driven by the SCW11 promoter (FIG. 4). Cells were washed, diluted and plated onto YPD agar plates for assessment of SCRaMbLE-induced lethality. All heterozygous diploid strains tested were substantially more tolerant of Cre-mediated SCRaMbLE compared to haploid strains (FIG. 1b,c). Inspection of the plated cells reveals an increase in the frequency of slow-growing colonies that arise upon estradiol pretreatment; such small colonies typically show rearrangements when they arise in the corresponding haploid strains, suggesting that SCRaMbLE is functioning in the wide range of strain backgrounds. We further confirmed that heterozygous diploid strains with two synthetic chromosomes were also capable of undergoing SCRaMbLE while displaying less recombinase-mediated cell death compared to haploid strains (FIG. 1c). We also did not notice any difference in behavior between heterozygous diploid strains constructed with S. cerevisiae strains from the SGRP and those constructed with S. paradoxus strains, suggesting that SCRaMbLE of heterozygous diploids can be applied to Saccharomyces interspecies strain combinations.

Example 2

Figure 2:
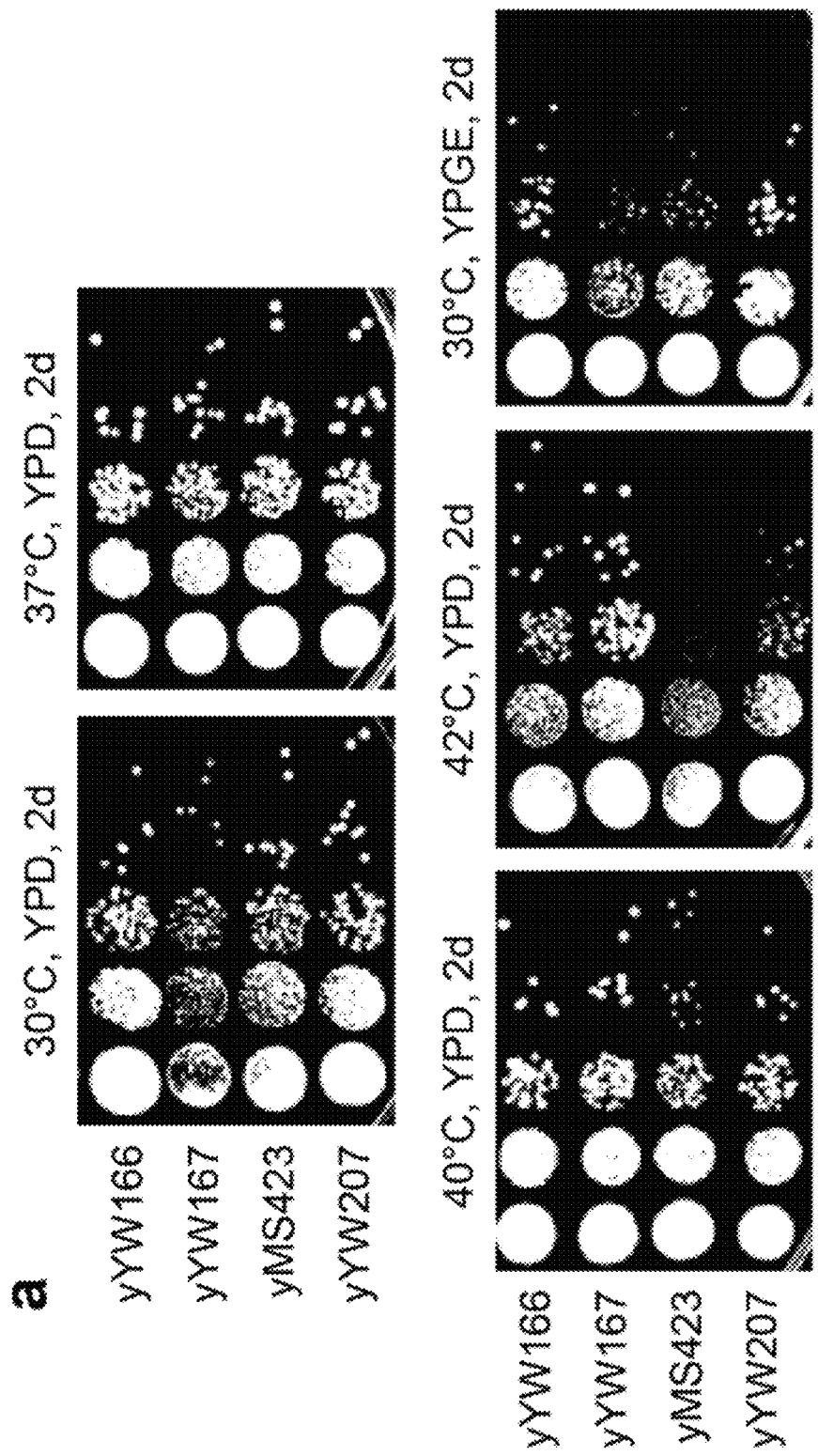
FIG. 2: SCRaMbLE of Y12-synX heterozygous diploids rapidly improves thermotolerance. (a) Serial dilution assay comparing the growth of two independent SCRaMbLEd isolates of Y12-synX (yYW166 and yYW167) with the non-SCRaMbLEd parent strain (yMS423) and a Y12 diploid strain (yYW207) under various temperature conditions as well as in YPGE. (b) Average sequencing depth per segment along synX of yMS423, yYW166, and yYW167. Deletions (boxes A, B, C, E, F, G, H, I, and J) as well as a duplication (box D) are highlighted. (c) Structural variation in yYW166 (blue) and yYW167 (red) reveals a common deletion of YJL154C-YJL140W among deletions ranging from 0.38 to 137 kb in length. The duplicated segment YJL027C-YJL022W is 6.5 kb in length.
Figure 2:
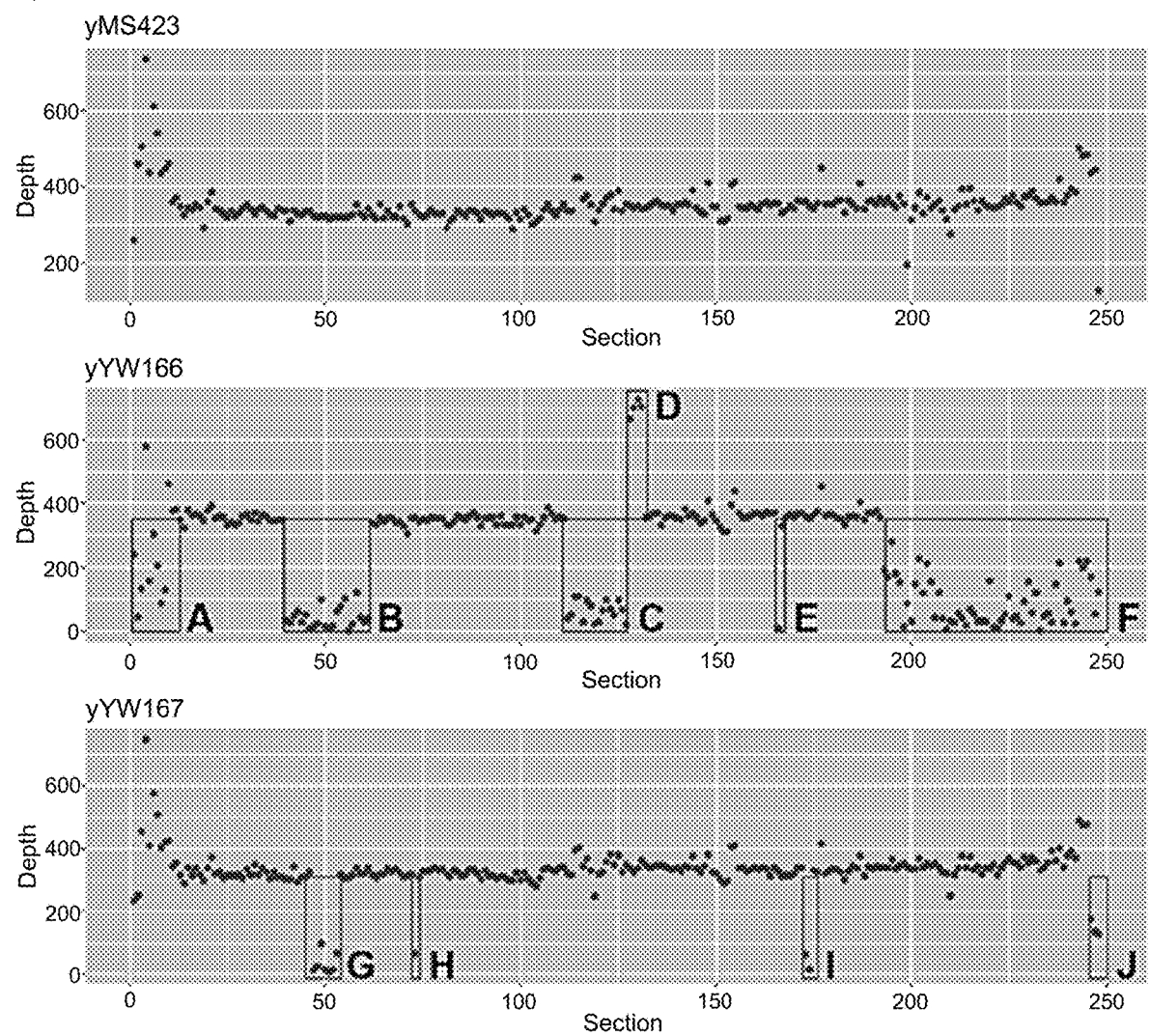

We next sought to determine whether SCRaMbLE could improve the ability of heterozygous diploid strains to tolerate extreme drug or environmental conditions. We examined a heterozygous diploid strain composed of the Y12 sake brewing S. cerevisiae strain mated with a synthetic chromosome X-bearing strain (Y12-synX). Y12 was chosen for its relative thermotolerance compared to other S. cerevisiae strains as well as its use in an industrially relevant process. Y12-synX cells were subjected to SCRaMbLE as described above and selected at 42° C. Thermotolerant colonies were grown in liquid YPD cultures with daily serial dilution for one week to ensure loss of the Cre plasmid and then grown at 30° C., 37° C., 40° C., and 42° C. Multiple independent SCRaMbLEd isolates displayed an improvement in growth at 42° C. when compared to parent non-SCRaMbLEd strains (FIG. 2a). Interestingly, isolates that grew well at 42° C. (yYW166, yYW167) displayed decreased fitness at both 30° C. and 37° C. compared to their non-SCRaMbLEd counterparts.

Example 3

We used whole genome sequencing to examine the recombination events that occurred in yYW166 and yYW167. Because SCRaMbLE events by nature act on the stretches of DNA between loxPsym sites as discrete units, we broke down synX into 248 segments, with each segment flanked by one (in the case of the first and last segments) or two loxPsym sites. By determining the emergence of novel junctions between non-adjacent segments and using average coverage across a segment to calculate its "copy number," we were able to infer some of the structural changes caused by SCRaMbLE. Our analysis showed that yYW166 had four deletions encompassing the ORFs YJL222W-YJL217W, YJL161W-YJL130C, YJL052C-YJL028W, and YJR093C-YJR159W, a smaller deletion not encompassing an ORF, and a duplication in the YJL027C-YJL022W region (FIG. 2b, c). yYW167 had two deletions spanning the ORFs YJL154C-YJL140W and YJR055W-YJR056C along with two smaller deletions. Deletion of the YJL154C-YJL140W region, spanning 20,815 bp, was common to both strains. This region includes TIM17 (YJL143W), an essential gene whose deletion would have been lethal had this SCRaMbLE event occurred in a semisynthetic haploid cell. These data provide evidence that multiple independent rearrangements can result in similar phenotypes in SCRaMbLEd heterozygous diploids and that SCRaMbLE of heterozygous diploids can recover genotypes that cannot be found by SCRaMbLE of semisynthetic haploids.

Example 4

Figure 3:
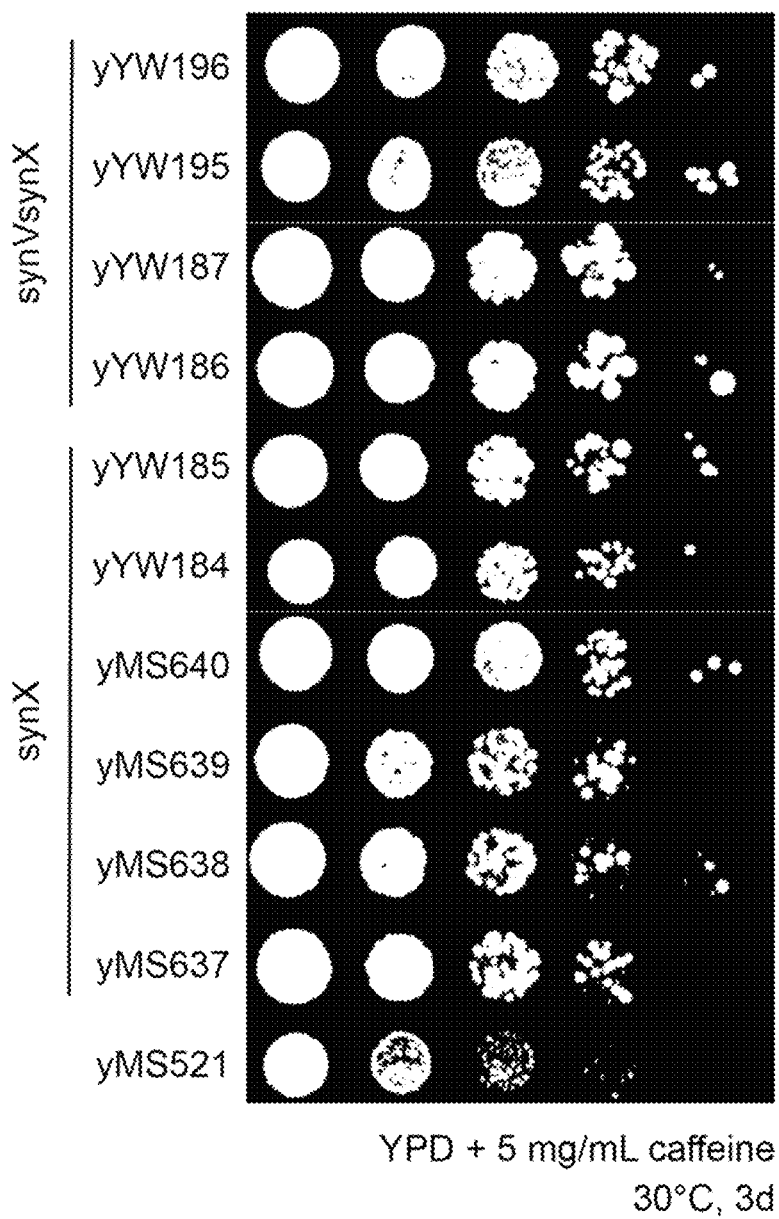
FIG. 3: SCRaMbLE of a *S. paradoxus* CBS5829-synX or CBS5829-synVsynX heterozygous diploid improves caffeine tolerance. (a) Serial dilution assay comparing the growth of SCRaMbLEd CBS5829-synX (yMS637, yMS638, yMS639, yMS640, yYW184, and yYW185) or CBS5829-synVsynX (yYW186, yYW187, yYW195, and yYW196) strains to their non-SCRaMbLEd CBS5829-synX parent (yMS521) on high caffeine YPD plates. (b) Whole genome sequencing analysis revealed a common duplication region in both the SCRaMbLEd strains yMS637 and yYW185 compared to their non-SCRaMbLEd parent yMS521. This region, spanning two loxPsym-flanked segments and just over 2 kb in length, contains the POL32 gene.
Figure 3:
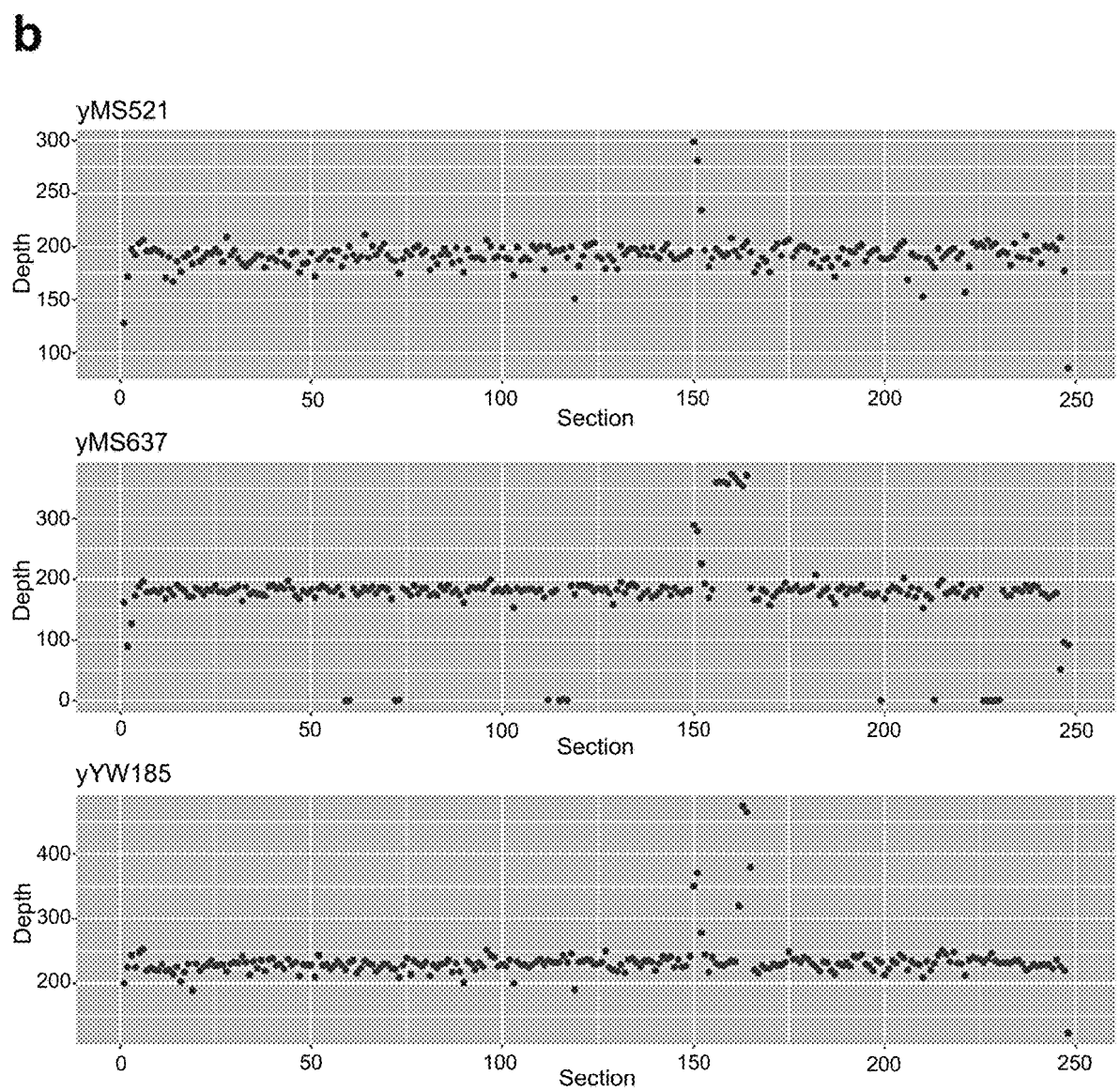
Figure 3:
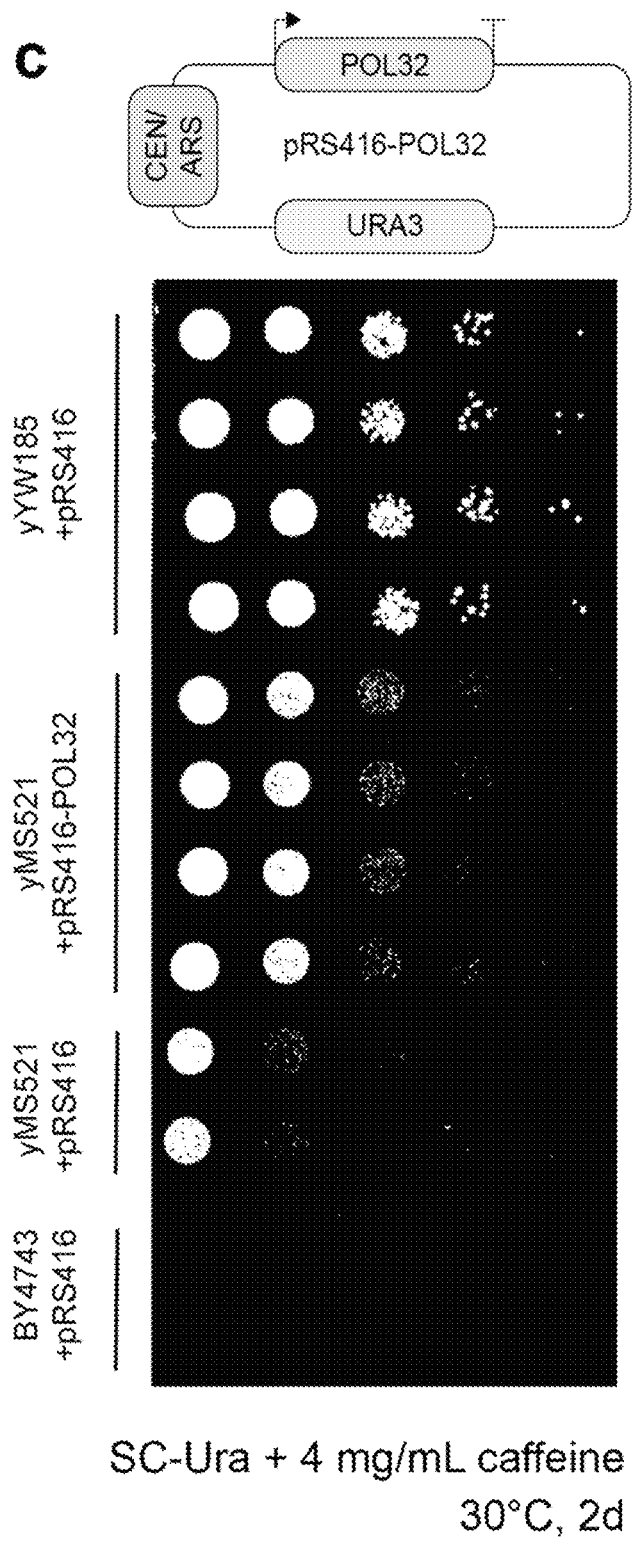

We chose a candidate comprised of the S. paradoxus strain CBS5829 mated with synX bearing strain (CBS5829-synX) based on the robust relative tolerance of CBS5829 to caffeine[8] as a non-limiting illustration of the present invention. Caffeine, in a similar fashion to the macrolide antibiotic rapamycin, is an inhibitor of the TOR kinase cascade in both budding yeast and the fission yeast Schizosaccharomyces pombe, leading to increased chronological lifespan[10,11]. We used a single 6-hour exposure of CBS5829-synX cells to β-estradiol to induce SCRaMbLE. We detected differential growth between SCRaMbLEd and non-SCRaMbLEd strains on liquid YPD containing 5 and 7 mg/mL caffeine, a phenotype that we subsequently verified on solid medium with serial dilution assays (FIG. 3a). Strains exhibiting caffeine-tolerant phenotypes were obtained in multiple independent SCRaMbLE experiments with selection either immediately post-SCRaMbLE on solid medium containing caffeine or in liquid YPD containing caffeine. We also SCRaMbLEd a CBS5829-synVsynX heterozygous diploid strain and assessed the resulting cells for caffeine tolerance. We were able to obtain isolates that showed a similar degree of caffeine resistance in both strains.

Example 5

We used whole genome sequencing to examine the changes caused by SCRaMbLE in independent isolates of caffeine tolerant heterozygous diploids. We were able to detect each of deletions, inversions, and duplications in SCRaMbLEd strains, with no two isolates having the same set of chromosomal rearrangements. We did, however, notice a duplication in two synX segments in two independent isolates obtained from independent experiments (FIG. 3b). This duplication, of synX segments 163 and 164, included POL32, a nonessential subunit of DNA polymerase $\delta$[12]. The duplication in the two strains was molecularly distinct, with one strain containing 7 adjacent upstream segments duplicated, and another containing one adjacent downstream segment duplicated. POL32 has been associated with roles in DNA damage repair and chromosomal DNA replication, and previous work examining POL32 null mutants has demonstrated an increased resistance to rapamycin[13]. Interestingly, and consistent with the earlier work, SCRaMbLEd strains with POL32 duplications seemed to be more sensitive to rapamycin than non- SCRaMbLEd parental strains (FIG. 5). Introducing an episomal copy of POL32 under its native promoter to the non-SCRaMbLEd CBS5829-synX strain was sufficient to increase its caffeine tolerance (FIG. 3c), although not to levels as high as SCRaMbLEd strains. This result points to the utility of heterozygous diploid SCRaMbLE in identifying genes previously unassociated with particular drug tolerances.

Example 6

We extended both phenotype testing and WGS analysis to a heterozygous diploid CBS5829-synVsynX containing two synthetic chromosomes. Initial SCRaMbLE of heterozygous diploids with two synthetic chromosomes also proved more robust than their haploid counterparts (data not shown). SCRaMbLE also increased the caffeine tolerance of CBS5829-synVsynX strains. From the 4 strains we sequenced, we did not observe conserved rearrangements in SCRaMbLEd CBS5829-synVsynX strains or rearrangements common to both CBS5829-synX and CBS5829-synVsynX strains.

Example 7

This Example provides a description of the materials and methods used to obtain the results of this disclosure.

Strains and Media

All yeast strains are described in Table 1 and 2. All synX and synVsynX containing strains are derived from BY4741 (MATa leu2Δ0 met15Δ0 ura3Δ0 his3Δ1). β-estradiol and caffeine were purchased from Sigma-Aldrich (St. Louis, MO). Rapamycin was purchased from EMD Millipore (Billerica, MA). Yeast strains were cultured in YPD medium or SC dropout plates supplemented with appropriate amino acids and/or drugs. Transformations were done using standard lithium acetate procedures.

To construct strains yYW168 and yYW169, the NatMX cassette was PCR amplified from pFA6a-5FLAG-natMX6 (Addgene, Cambridge, MA) using Phusion DNA polymerase (New England Biolabs, Ipswich, MA) and primers (Integrated DNA Technologies, Coralville, IA) including homology upstream and downstream of the LYS2 coding sequence. The resulting amplicon was purified with the DNA Clean and Concentrator-5 kit (Zymo Research, Irvine, CA), transformed into yYW117 and yYW139 and plated on YEPD plates. The resulting transformants were replica plated onto YPD plates containing 0.1 mg/mL clonNAT (Gold biotechnology, St. Louis, MO) to select for Nat® colonies.

Haploid MATα strains from the *Saccharomyces* Genome Resequencing Project (SGRP) were purchased from the National Collection of Yeast Cultures (Norwich, UK). Each heterozygous diploid strain was constructed by mating either yYW168 or yYW169 (both MATα) to the appropriate MATα SGRP strain. The resulting diploid cells were selected on YPD plates containing 0.1 mg/mL clonNAT and 0.2 mg/mL G418 (Santa Cruz Biotechnology, Dallas, TX).

Cloning was done in Top10 *Escherichia coli* grown in Luria Broth (LB) media. To select strains with drug-resistant genes, carbenicillin (Sigma-Aldrich) was used at a final concentration of 75 µg/ml. Agar was added to 2% for preparing solid media.

Plasmids

The POL32 coding sequence was PCR amplified from BY4741 genomic DNA with 500 bp upstream and 300 bp downstream sequence using Phusion DNA polymerase (New England Biolabs). The resulting amplicon was digested with BamHI and EcoRI (New England Biolabs), gel purified (Zymo Research), and cloned into pRS416 to create pRS416-POL32.

SCRaMbLE of Heterozygous Diploids

Heterozygous diploid cells were transformed with pRS416-pCLB2-CreEBD and maintained on SC-Ura plates. Cells were grown overnight in liquid SC-Ura media to saturation. Cultures were diluted to a starting OD of 0.1 in 50 mL of fresh liquid SC-Ura media. β-estradiol was added to a final concentration of 1 µM and cultures were incubated at 30° C. with shaking at 225 RPM for 6 hours. Cultures were spun down at 3000 RPM for 3 minutes and washed three times with water to wash out β-estradiol and cells were plated onto either solid YPD medium or solid YPD medium containing a selective agent.

Genomic DNA Preparation

To prepare genomic DNA, we used the Norgen Fungi/Yeast genomic DNA isolation kit (Norgen Biotek, Ontario, Canada) according to the manufacturer's instructions.

Whole Genome Sequencing

Paired-end whole genome sequencing was performed using an Illumina 4000 system with TruSeq library preparation kits. The length of each read was 151 base pairs. Quality control was performed using Trimmomatic 0.33 with the parameters LEADING:3 TRAILING:3 SLIDINGWINDOW:4:15 MINLEN:75. Alignments to a custom-made reference genome were done using bowtie2 (2.2.9) software.

Detection of SCRaMbLE Events and Coverage

A custom Ruby and Python pipeline based on the reference of Y. Shen et al.[20] was employed to detect SCRaMbLE events. First, unmapped reads containing loxPsym sites were aggregated, and those with fewer than 20 bp on either side of the loxPsym site were discarded. Reads were then trisected into three parts: the left arm, the loxPsym site, and the right arm. The synthetic chromosome was broken up into segments, with each segment spanning the base pairs between two loxPsym sites (i.e. segment 1 includes bases from bp 1 up until the first loxPsym site, segment 2 from after the first loxPsym up until the second loxPsym site, etc.). The Smith-Waterman local alignment algorithm was used to map the left arm and right arm to segments on the synthetic chromosome and establish "new" junctions. Additionally, the average coverage across each segment was calculated by summing the coverage at each position in the segment and dividing by the segment length. For SCRaMbLEd strains, this value was compared to that of the non-SCRaMbLEd parent to determine changes in copy number. Segment copy number and "new" junctions were used to determine SCRaMbLE events that occurred.

TABLE 1

Strains of this disclosures

| Strain Name | Description | Genotype |
|---|---|---|
| BY4741 | | Mata his3Δ1 leu2Δ0 met15Δ0 ura3Δ0 |
| BY4743 | | MATa/α his3Δ1/his3Δ1 leu2Δ0/leu2Δ0 LYS2/lys2Δ0 met15Δ0/MET15 ura3Δ0/ura3Δ0 |
| yYW117 | BY4741 containing synX | MATa his3Δ1 leu2Δ0 met15Δ0 ura3Δ0 SYN10 ho::tR(ccu)J |
| yYW168 | synX lys2::NatMX | MATa his3Δ1 leu2Δ0 met15Δ0 ura3Δ0 SYN10 ho::tR(ccu)J lys2::NatMX |
| yYW139 | BY4741 containing synVsynX | MATa his3Δ1 leu2Δ0 met15Δ0 ura3Δ0 SYN5 SYN10 ho::tR(ccu)J |
| yYW169 | synVX lys2::NatMX | MATa his3Δ1 leu2Δ0 met15Δ0 ura3Δ0 SYN5 SYN10 ho::tR(ccu)J lys2::NatMX |
| yMS253 | S288C alpha haploid | MATα ura3::KanMX ho::Hyg |
| yMS275 | Y12 alpha haploid | MATα ura3::KanMX ho::Hyg |
| yMS354 | CBS5829 alpha haploid | MATα ura3::KanMX ho::Hyg |
| yYW207 | Y12 diploid | MATa/α ura3::KanMX/ura3::KanMX ho::Hyg/ho::Hyg |
| yYW208 | CBS5829 diploid | MATa/α ura3::KanMX/ura3::KanMX ho::Hyg/ho::Hyg |
| yMS401 | Diploid of yYW168 and yMS253 | MATa/α ura3Δ0/ura3::KanMX ho::tR(ccu)J/ho::Hyg lys2::NatMX/LYS2 SYN10/WT10 |
| yMS426 | Diploid of yYW169 and yMS253 | MATa/α ura3Δ0/ura3::KanMX ho::tR(ccu)J/ho::Hyg lys2::NatMX/LYS2 SYN5/WT5 SYN10/WT10 |
| yMS423 | Diploid of yYW168 and yMS275 | MATa/α ura3Δ0/ura3::KanMX ho::tR(ccu)J/ho::Hyg lys2::NatMX/LYS2 SYN10/WT10 |
| yMS448 | Diploid of yYW169 and yMS275 | MATa/α ura3Δ0/ura3::KanMX ho::tR(ccu)J/ho::Hyg lys2::NatMX/LYS2 SYN5/WT5 SYN10/WT10 |
| yMS521 | Diploid of yYW168 and yMS354 | MATa/α ura3Δ0/ura3::KanMX ho::tR(ccu)J/ho::Hyg lys2::NatMX/LYS2 SYN10/WT10 |
| yMS548 | Diploid of yYW169 and yMS354 | MATa/α ura3Δ0/ura3::KanMX ho::tR(ccu)J/ho::Hyg lys2::NatMX/LYS2 SYN5/WT5 SYN10/WT10 |
| yYW166 | yMS423, SCRaMbLEd, heat tolerant | MATa/α ura3Δ0/ura3::KanMX ho::tR(ccu)J/ho::Hyg lys2::NatMX/LYS2 SYN10/WT10 |
| yYW167 | yMS423, SCRaMbLEd, heat tolerant | MATa/α ura3Δ0/ura3::KanMX ho::tR(ccu)J/ho::Hyg lys2::NatMX/LYS2 SYN10/WT10 |
| yYW184 | yMS521, SCRaMbLEd, caffeine tolerant | MATa/α ura3Δ0/ura3::KanMX ho::tR(ccu)J/ho::Hyg lys2::NatMX/LYS2 SYN10/WT10 |
| yYW185 | yMS521, SCRaMbLEd, caffeine tolerant | MATa/α ura3Δ0/ura3::KanMX ho::tR(ccu)J/ho::Hyg lys2::NatMX/LYS2 SYN10/WT10 |
| yYW186 | yMS548, SCRaMbLEd, caffeine tolerant | MATa/α ura3Δ0/ura3::KanMX ho::tR(ccu)J/ho::Hyg lys2::NatMX/LYS2 SYN5/WT5 SYN10/WT10 |
| yYW187 | yMS548, SCRaMbLEd, caffeine tolerant | MATa/α ura3Δ0/ura3::KanMX ho::tR(ccu)J/ho::Hyg lys2::NatMX/LYS2 SYN5/WT5 SYN10/WT10 |
| yYW195 | yMS548, SCRaMbLEd, caffeine tolerant | MATa/α ura3Δ0/ura3::KanMX ho::tR(ccu)J/ho::Hyg lys2::NatMX/LYS2 SYN5/WT5 SYN10/WT10 |
| yYW196 | yMS548, SCRaMbLEd, caffeine tolerant | MATa/α ura3Δ0/ura3::KanMX ho::tR(ccu)J/ho::Hyg lys2::NatMX/LYS2 SYN5/WT5 SYN10/WT10 |
| yMS637 | yMS521, SCRaMbLEd, caffeine tolerant | MATa/α ura3Δ0/ura3::KanMX ho::tR(ccu)J/ho::Hyg lys2::NatMX/LYS2 SYN10/WT10 |
| yMS638 | yMS521, SCRaMbLEd, caffeine tolerant | MATa/α ura3Δ0/ura3::KanMX ho::tR(ccu)J/ho::Hyg lys2::NatMX/LYS2 SYN10/WT10 |
| yMS639 | yMS521, SCRaMbLEd, caffeine tolerant | MATa/α ura3Δ0/ura3::KanMX ho::tR(ccu)J/ho::Hyg lys2::NatMX/LYS2 SYN10/WT10 |
| yMS640 | yMS521, SCRaMbLEd caffeine tolerant | MATa/α ura3Δ0/ura3::KanMX ho::tR(ccu)J/ho::Hyg lys2::NatMX/LYS2 SYN10/WT10 |
| yMS674 | yMS521 + episomal POL32 | MATa/α ura3Δ0/ura3::KanMX ho::tR(ccu)J/ho::Hyg lys2::NatMX/LYS2 SYN10/WT10 |
| yMS675 | yMS521 + episomal POL32 | MATa/α ura3Δ0/ura3::KanMX ho::tR(ccu)J/ho::Hyg lys2::NatMX/LY52 SYN10/WT10 |

TABLE 2

List of heterozygous diploid strains. Bold strains were used in this disclosure.

| Strain Name | Description | Genotype |
|---|---|---|
| yMS401 | synX and S288c | MATa/α ura3Δ0/ura3::KanMX ho::tR(ccu)J/ho::Hyg lys2::NatMX/LYS2 SYN10/WT10 |
| yMS402 | synX and UWOPS87-2421 | MATa/α ura3Δ0/ura3::KanMX ho::tR(ccu)J/ho::Hyg lys2::NatMX/LYS2 SYN10/WT10 |
| yMS403 | synX and 378604X | MATa/α ura3Δ0/ura3::KanMX ho::tR(ccu)J/ho::Hyg lys2::NatMX/LYS2 SYN10/WT10 |
| yMS404 | synX and 273614N | MATa/α ura3Δ0/ura3::KanMX ho::tR(ccu)J/ho::Hyg lys2::NatMX/LYS2 SYN10/WT10 |
| yMS405 | synX and YIIc17_E5 | MATa/α ura3Δ0/ura3::KanMX ho::tR(ccu)J/ho::Hyg lys2::NatMX/LYS2 SYN10/WT10 |

TABLE 2-continued

List of heterozygous diploid strains. Bold strains were used in this disclosure.

| Strain Name | Description | Genotype |
| --- | --- | --- |
| yMS406 | synX and Y55 | MATa/α ura3Δ0/ura3::KanMX ho::tR(ccu)J/ho::Hyg lys2::NatMX/LYS2 SYN10/WT10 |
| yMS407 | synX and UWOPS83-787.3 | MATa/α ura3Δ0/ura3::KanMX ho::tR(ccu)J/ho::Hyg lys2::NatMX/LYS2 SYN10/WT10 |
| yMS408 | synX and SK1 | MATa/α ura3Δ0/ura3::KanMX ho::tR(ccu)J/ho::Hyg lys2::NatMX/LYS2 SYN10/WT10 |
| yMS409 | synX and BC187 | MATa/α ura3Δ0/ura3::KanMX ho::tR(ccu)J/ho::Hyg lys2::NatMX/LYS2 SYN10/WT10 |
| yMS410 | synX and YJM978 | MATa/α ura3Δ0/ura3::KanMX ho::tR(ccu)J/ho::Hyg lys2::NatMX/LYS2 SYN10/WT10 |
| yMS411 | synX and YJM981 | MATa/α ura6Δ0/ura3::KanMX ho::tR(ccu)J/ho::Hyg lys2::NatMX/LYS2 SYN10/WT10 |
| yMS412 | synX and YJM975 | MATa/α ura3Δ0/ura3::KanMX ho::tR(ccu)J/ho::Hyg lys2::NatMX/LYS2 SYN10/WT10 |
| yMS413 | synX and DBVPG 1373 | MATa/α ura3Δ0/ura3::KanMX ho::tR(ccu)J/ho::Hyg lys2::NatMX/LYS2 SYN10/WT10 |
| yMS414 | synX and DBVPG 1106 | MATa/α ura3Δ0/ura3::KanMX ho::tR(ccu)J/ho::Hyg lys2::NatMX/LYS2 SYN10/WT10 |
| yMS415 | synX and DBVPG 6765 | MATa/α ura3Δ0/ura3::KanMX ho::tR(ccu)J/ho::Hyg lys2::NatMX/LYS2 SYN10/WT10 |
| yMS416 | synX and L_1374 | MATa/α ura3Δ0/ura3::KanMX ho::tR(ccu)J/ho::Hyg lys2::NatMX/LYS2 SYN10/WT10 |
| yMS417 | synX and L_1528 | MATa/α ura3Δ0/ura3::KanMX ho::tR(ccu)J/ho::Hyg lys2::NatMX/LYS2 SYN10/WT10 |
| yMS418 | synX and DBVPG 6044 | MATa/α ura3Δ0/ura3::KanMX ho::tR(ccu)J/ho::Hyg lys2::NatMX/LYS2 SYN10/WT10 |
| yMS419 | synX and NCYC 110 | MATa/α ura3Δ0/ura3::KanMX ho::tR(ccu)J/ho::Hyg lys2::NatMX/LYS2 SYN10/WT10 |
| yMS420 | synX and UWOPS03-461.4 | MATa/α ura3Δ0/ura3::KanMX ho::tR(ccu)J/ho::Hyg lys2::NatMX/LYS2 SYN10/WT10 |
| yMS421 | synX and UWOPS05-217.3 | MATa/α ura3Δ0/ura3::KanMX ho::tR(ccu)J/ho::Hyg lys2::NatMX/LYS2 SYN10/WT10 |
| yMS422 | synX and UWOPS05-227.2 | MATa/α ura3Δ0/ura3::KanMX ho::tR(ccu)J/ho::Hyg lys2::NatMX/LYS2 SYN10/WT10 |
| yMS423 | synX and Y12 | MATa/α ura3Δ0/ura3::KanMX ho::tR(ccu)J/ho::Hyg lys2::NatMX/LYS2 SYN10/WT10 |
| yMS424 | synX and YPS606 | MATa/α ura3Δ0/ura3::KanMX ho::tR(ccu)J/ho::Hyg lys2::NatMX/LYS2 SYN10/WT10 |
| yMS425 | synX and YPS128 | MATa/α ura3Δ0/ura3::KanMX ho::tR(ccu)J/ho::Hyg lys2::NatMX/LYS2 SYN10/WT10 |
| yMS426 | synVsynX and S288c | MATa/α ura3Δ0/ura3::KanMX ho::tR(ccu)J/ho::Hyg lys2::NatMX/LYS2 SYN5/WT5 SYN10/WT10 |
| yMS427 | synVsynX and UWOPS87-2421 | MATa/α ura3Δ0/ura3::KanMX ho::tR(ccu)J/ho::Hyg lys2::NatMX/LYS2 SYN5/WT5 SYN10/WT10 |
| yMS428 | synVsynX and 378604X | MATa/α ura3Δ0/ura3::KanMX ho::tR(ccu)J/ho::Hyg lys2::NatMX/LYS2 SYN5/WT5 SYN10/WT10 |
| yMS429 | synVsynX and 273614N | MATa/α ura3Δ0/ura3::KanMX ho::tR(ccu)J/ho::Hyg lys2::NatMX/LYS2 SYN5/WT5 SYN10/WT10 |
| yMS430 | synVsynX and YIIc17_E5 | MATa/α ura3Δ0/ura3::KanMX ho::tR(ccu)J/ho::Hyg lys2::NatMX/LYS2 SYN5/WT5 SYN10/WT10 |
| yMS431 | synVsynX and Y55 | MATa/α ura3Δ0/ura3::KanMX ho::tR(ccu)J/ho::Hyg lys2::NatMX/LYS2 SYN5/WT5 SYN10/WT10 |
| yMS432 | synVsynX and UWOPS83-787.3 | MATa/α ura3Δ0/ura3::KanMX ho::tR(ccu)J/ho::Hyg lys2::NatMX/LYS2 SYN5/WT5 SYN10/WT10 |
| yMS433 | synVsynX and SK1 | MATa/α ura3Δ0/ura3::KanMX ho::tR(ccu)J/ho::Hyg lys2::NatMX/LYS2 SYN5/WT5 SYN10/WT10 |
| yMS434 | synVsynX and BC187 | MATa/α ura3Δ0/ura3::KanMX ho::tR(ccu)J/ho::Hyg lys2::NatMX/LYS2 SYN5/WT5 SYN10/WT10 |
| yMS435 | synVsynX and YJM978 | MATa/α ura3Δ0/ura3::KanMX ho::tR(ccu)J/ho::Hyg lys2::NatMX/LYS2 SYN5/WT5 SYN10/WT10 |
| yMS436 | synVsynX and YJM981 | MATa/α ura3Δ0/ura3::KanMX ho::tR(ccu)J/ho::Hyg lys2::NatMX/LYS2 SYN5/WT5 SYN10/WT10 |
| yMS437 | synVsynX and YJM975 | MATa/α ura3Δ0/ura3::KanMX ho::tR(ccu)J/ho::Hyg lys2::NatMX/LYS2 SYN5/WT5 SYN10/WT10 |
| yMS438 | synVsynX and DBVPG 1373 | MATa/α ura3Δ0/ura3::KanMX ho::tR(ccu)J/ho::Hyg lys2::NatMX/LYS2 SYN5/WT5 SYN10/WT10 |
| yMS439 | synVsynX and DBVPG 1106 | MATa/α ura3Δ0/ura3::KanMX ho::tR(ccu)J/ho::Hyg lys2::NatMX/LYS2 SYN5/WT5 SYN10/WT10 |
| yMS440 | synVsynX and DBVPG 6765 | MATa/α ura3Δ0/ura3::KanMX ho::tR(ccu)J/ho::Hyg lys2::NatMX/LYS2 SYN5/WT5 SYN10/WT10 |
| yMS441 | synVsynX and L_1374 | MATa/α ura3Δ0/ura3::KanMX ho::tR(ccu)J/ho::Hyg lys2::NatMX/LYS2 SYN5/WT5 SYN10/WT10 |
| yMS442 | synVsynX and L_1528 | MATa/α ura3Δ0/ura3::KanMX ho::tR(ccu)J/ho::Hyg lys2::NatMX/LYS2 SYN5/WT5 SYN10/WT10 |
| yMS443 | synVsynX and DBVPG 6044 | MATa/α ura3Δ0/ura3::KanMX ho::tR(ccu)J/ho::Hyg lys2::NatMX/LYS2 SYN5/WT5 SYN10/WT10 |

TABLE 2-continued

List of heterozygous diploid strains. Bold strains were used in this disclosure.

| Strain Name | Description | Genotype |
| --- | --- | --- |
| yMS444 | synVsynX and NCYC 110 | MATa/α ura3Δ0/ura3::KanMX ho::tR(ccu)J/ho::Hyg lys2::NatMX/LYS2 SYN5/WT5 SYN10/WT10 |
| yMS445 | synVsynX and UWOPS03-461.4 | MATa/α ura3Δ0/ura3::KanMX ho::tR(ccu)J/ho::Hyg lys2::NatMX/LYS2 SYN5/WT5 SYN10/WT10 |
| yMS446 | synVsynX and UWOPS05-217.3 | MATa/α ura3Δ0/ura3::KanMX ho::tR(ccu)J/ho::Hyg lys2::NatMX/LYS2 SYN5/WT5 SYN10/WT10 |
| yMS447 | synVsynX and UWOPS05-227.2 | MATa/α ura3Δ0/ura3::KanMX ho::tR(ccu)J/ho::Hyg lys2::NatMX/LYS2 SYN5/WT5 SYN10/WT10 |
| yMS448 | synVsynX and Y12 | MATa/α ura3Δ0/ura3::KanMX ho::tR(ccu)J/ho::Hyg lys2::NatMX/LYS2 SYN5/WT5 SYN10/WT10 |
| yMS449 | synVsynX and YPS606 | MATa/α ura3Δ0/ura3::KanMX ho::tR(ccu)J/ho::Hyg lys2::NatMX/LYS2 SYN5/WT5 SYN10/WT10 |
| yMS450 | synVsynX and YPS128 | MATa/α ura3Δ0/ura3::KanMX ho::tR(ccu)J/ho::Hyg lys2::NatMX/LYS2 SYN5/WT5 SYN10/WT10 |
| yMS501 | synX and CBS432 | MATa/α ura3Δ0/ura3::KanMX ho::tR(ccu)J/ho::Hyg lys2::NatMX/LYS2 SYN10/WT10 |
| yMS502 | synX and T21.4 | MATa/α ura3Δ0/ura3::KanMX ho::tR(ccu)J/ho::Hyg lys2::NatMX/LYS2 SYN10/WT10 |
| yMS503 | synX and Y7 | MATa/α ura3Δ0/ura3::KanMX ho::tR(ccu)J/ho::Hyg lys2::NatMX/LYS2 SYN10/MT10 |
| yMS504 | synX and Q32.3 | MATa/α ura3Δ0/ura3::KanMX ho::tR(ccu)J/ho::Hyg lys2::NatMX/LYS2 SYN10/WT10 |
| yMS505 | synX and Q59.1 | MATa/α ura3Δ0/ura3::KanMX ho::tR(ccu)J/ho::Hyg lys2::NatMX/LYS2 SYN10/WT10 |
| yMS506 | synX and Q95.3 | MATa/α ura3Δ0/ura3::KanMX ho::tR(ccu)J/ho::Hyg lys2::NatMX/LYS2 SYN10/WT10 |
| yMS507 | synX and S36.7 | MATa/α ura3Δ0/ura3::KanMX ho::tR(ccu)J/ho::Hyg lys2::NatMX/LYS2 SYN10/MT10 |
| yMS508 | synX and Z1.1 | MATa/α ura3Δ0/ura3::KanMX ho::tR(ccu)J/ho::Hyg lys2::NatMX/LYS2 SYN10/WT10 |
| yMS509 | synX and Y6.5 | MATa/α ura3Δ0/ura3::KanMX ho::tR(ccu)J/ho::Hyg lys2::NatMX/LYS2 SYN10/WT10 |
| yMS510 | synX and Q62.5 | MATa/α ura3Δ0/ura3::KanMX ho::tR(ccu)J/ho::Hyg lys2::NatMX/LYS2 SYN10/WT10 |
| yMS511 | synX and Q89.8 | MATa/α ura3Δ0/ura3::KanMX ho::tR(ccu)J/ho::Hyg lys2::NatMX/LYS2 SYN10/MT10 |
| yMS512 | synX and Y9.6 | MATa/α ura3Δ0/ura3::KanMX ho::tR(ccu)J/ho::Hyg lys2::NatMX/LYS2 SYN10/WT10 |
| yMS513 | synX and Q74.4 | MATa/α ura3Δ0/ura3::KanMX ho::tR(ccu)J/ho::Hyg lys2::NatMX/LYS2 SYN10/WT10 |
| yMS514 | synX and Q69.8 | MATa/α ura3Δ0/ura3::KanMX ho::tR(ccu)J/ho::Hyg lys2::NatMX/LYS2 SYN10/WT10 |
| yMS515 | synX and W7 | MATa/α ura3Δ0/ura3::KanMX ho::tR(ccu)J/ho::Hyg lys2::NatMX/LYS2 SYN10/WT10 |
| yMS516 | synX and Q31.4 | MATa/α ura3Δ0/ura3::KanMX ho::tR(ccu)J/ho::Hyg lys2::NatMX/LYS2 SYN10/WT10 |
| yMS517 | synX and Y8.5 | MATa/α ura3Δ0/ura3::KanMX ho::tR(ccu)J/ho::Hyg lys2::NatMX/LYS2 SYN10/WT10 |
| yMS518 | synX and Z1.1 | MATa/α ura3Δ0/ura3::KanMX ho::tR(ccu)J/ho::Hyg lys2::NatMX/LYS2 SYN10/WT10 |
| yMS519 | synX and Y8.1 | MATa/α ura3Δ0/ura3::KanMX ho::tR(ccu)J/ho::Hyg lys2::NatMX/LYS2 SYN10/WT10 |
| yMS520 | synX and N-17 | MATa/α ura3Δ0/ura3::KanMX ho::tR(ccu)J/ho::Hyg lys2::NatMX/LYS2 SYN10/WT10 |
| yMS521 | synX and CBS 5829 | MATa/α ura3Δ0/ura3::KanMX ho::tR(ccu)J/ho::Hyg lys2::NatMX/LYS2 SYN10/WT10 |
| yMS522 | synX and KPN3829 | MATa/α ura3Δ0/ura3::KanMX ho::tR(ccu)J/ho::Hyg lys2::NatMX/LYS2 SYN10/WT10 |
| yMS523 | synX and YPS138 | MATa/α ura3Δ0/ura3::KanMX ho::tR(ccu)J/ho::Hyg lys2::NatMX/LYS2 SYN10/WT10 |
| yMS524 | synX and DBVPG 6304 | MATa/α ura3Δ0/ura3::KanMX ho::tR(ccu)J/ho::Hyg lys2::NatMX/LYS2 SYN10/WT10 |
| yMS525 | synX and A12 | MATa/α ura3Δ0/ura3::KanMX ho::tR(ccu)J/ho::Hyg lys2::NatMX/LYS2 SYN10/WT10 |
| yMS526 | synX and N-44 | MATa/α ura3Δ0/ura3::KanMX ho::tR(ccu)J/ho::Hyg lys2::NatMX/LYS2 SYN10/WT10 |
| yMS527 | synX and IFO 1804 | MATa/α ura3Δ0/ura3::KanMX ho::tR(ccu)J/ho::Hyg lys2::NatMX/LYS2 SYN10/WT10 |
| yMS528 | synVsynX and CBS432 | MATa/α ura3Δ0/ura3::KanMX ho::tR(ccu)J/ho::Hyg lys2::NatMX/LYS2 SYN5/WT5 SYN10/WT10 |
| yMS529 | synVsynX and T21.4 | MATa/α ura3Δ0/ura3::KanMX ho::tR(ccu)J/ho::Hyg lys2::NatMX/LYS2 SYN5/WT5 SYN10/WT10 |
| yMS530 | synVsynX and Y7 | MATa/α ura3Δ0/ura3::KanMX ho::tR(ccu)J/ho::Hyg lys2::NatMX/LYS2 SYN5/WT5 SYN10/WT10 |
| yMS531 | synVsynX and Q32.3 | MATa/α ura3Δ0/ura3::KanMX ho::tR(ccu)J/ho::Hyg lys2::NatMX/LYS2 SYN5/WT5 SYN10/WT10 |

TABLE 2-continued

List of heterozygous diploid strains. Bold strains were used in this disclosure.

| Strain Name | Description | Genotype |
|---|---|---|
| yMS532 | synVsynX and Q59.1 | MATa/α ura3Δ0/ura3::KanMX ho::tR(ccu)J/ho::Hyg lys2::NatMX/LYS2 SYN5/WT5 SYN10/WT10 |
| yMS533 | synVsynX and Q95.3 | MATa/α ura3Δ0/ura3::KanMX ho::tR(ccu)J/ho::Hyg lys2::NatMX/LYS2 SYN5/WT5 SYN10/WT10 |
| yMS534 | synVsynX and S36.7 | MATa/α ura3Δ0/ura3::KanMX ho::tR(ccu)J/ho::Hyg lys2::NatMX/LYS2 SYN5/WT5 SYN10/WT10 |
| yMS535 | synVsynX and Z1.1 | MATa/α ura3Δ0/ura3::KanMX ho::tR(ccu)J/ho::Hyg lys2::NatMX/LYS2 SYN5/WT5 SYN10/WT10 |
| yMS536 | synVsynX and Y6.5 | MATa/α ura3Δ0/ura3::KanMX ho::tR(ccu)J/ho::Hyg lys2::NatMX/LYS2 SYN5/WT5 SYN10/WT10 |
| yMS537 | synVsynX and Q62.5 | MATa/α ura3Δ0/ura3::KanMX ho::tR(ccu)J/ho::Hyg lys2::NatMX/LYS2 SYN5/WT5 SYN10/WT10 |
| yMS538 | synVsynX and Q89.8 | MATa/α ura3Δ0/ura3::KanMX ho::tR(ccu)J/ho::Hyg lys2::NatMX/LYS2 SYN5/WT5 SYN10/WT10 |
| yMS539 | synVsynX and Y9.6 | MATa/α ura3Δ0/ura3::KanMX ho::tR(ccu)J/ho::Hyg lys2::NatMX/LYS2 SYN5/WT5 SYN10/WT10 |
| yMS540 | synVsynX and Q74.4 | MATa/α ura3Δ0/ura3::KanMX ho::tR(ccu)J/ho::Hyg lys2::NatMX/LYS2 SYN5/WT5 SYN10/WT10 |
| yMS541 | synVsynX and Q69.8 | MATa/α ura3Δ0/ura3::KanMX ho::tR(ccu)J/ho::Hyg lys2::NatMX/LYS2 SYN5/WT5 SYN10/WT10 |
| yMS542 | synVsynX and W7 | MATa/α ura3Δ0/ura3::KanMX ho::tR(ccu)J/ho::Hyg lys2::NatMX/LYS2 SYN5/WT5 SYN10/WT10 |
| yMS543 | synVsynX and Q31.4 | MATa/α ura3Δ0/ura3::KanMX ho::tR(ccu)J/ho::Hyg lys2::NatMX/LYS2 SYN5/WT5 SYN10/WT10 |
| yMS544 | synVsynX and Y8.5 | MATa/α ura3Δ0/ura3::KanMX ho::tR(ccu)J/ho::Hyg lys2::NatMX/LYS2 SYN5/WT5 SYN10/WT10 |
| yMS545 | synVsynX and Z1.1 | MATa/α ura3Δ0/ura3::KanMX ho::tR(ccu)J/ho::Hyg lys2::NatMX/LYS2 SYN5/WT5 SYN10/WT10 |
| yMS546 | synVsynX and Y8.1 | MATa/α ura3Δ0/ura3::KanMX ho::tR(ccu)J/ho::Hyg lys2::NatMX/LYS2 SYN5/WT5 SYN10/WT10 |
| yMS547 | synVsynX and N-17 | MATa/α ura3Δ0/ura3::KanMX ho::tR(ccu)J/ho::Hyg lys2::NatMX/LYS2 SYN5/WT5 SYN10/WT10 |
| yMS548 | synVsynX and CBS 5829 | MATa/α ura3Δ0/ura3::KanMX ho::tR(ccu)J/ho::Hyg lys2::NatMX/LYS2 SYN5/WT5 SYN10/WT10 |
| yMS549 | synVsynX and KPN3829 | MATa/α ura3Δ0/ura3::KanMX ho::tR(ccu)J/ho::Hyg lys2::NatMX/LYS2 SYN5/WT5 SYN10/WT10 |
| yMS550 | synVsynX and YPS138 | MATa/α ura3Δ0/ura3::KanMX ho::tR(ccu)J/ho::Hyg lys2::NatMX/LYS2 SYN5/WT5 SYN10/WT10 |
| yMS551 | synVsynX and DBVPG 6304 | MATa/α ura3Δ0/ura3::KanMX ho::tR(ccu)J/ho::Hyg lys2::NatMX/LYS2 SYN5/WT5 SYN10/WT10 |
| yMS552 | synVsynX and A12 | MATa/α ura3Δ0/ura3::KanMX ho::tR(ccu)J/ho::Hyg lys2::NatMX/LYS2 SYN5/WT5 SYN10/WT10 |
| yMS553 | synVsynX and N-44 | MATa/α ura3Δ0/ura3::KanMX ho::tR(ccu)J/ho::Hyg lys2::NatMX/LYS2 SYN5/WT5 SYN10/WT10 |
| yMS554 | synVsynX and IFO 1804 | MATa/α ura3Δ0/ura3::KanMX ho::tR(ccu)J/ho::Hyg lys2::NatMX/LYS2 SYN5/WT5 SYN10/WT10 |

TABLE 3

Inferred rearrangements in SCRaMbLEd strains

| strain | segment 1 | segment 2 | depth | inferred rearrangement |
|---|---|---|---|---|
| yMS637 | 10.129 | 10.-96 | 52 | inversion |
|  | 10.131 | 10.97 | 52 |  |
|  | 10.-113 | 10.-111 | 52 | deletion of segment 112 |
|  | 10.-231 | 10.-225 | 51 | deletion of segments 226-230 |
|  | 10.-61 | 10.-58 | 47 | deletion of segments 59 and 60 |
|  | 10.-132 | 10.13 | 45 | inversion |
|  | 10.-74 | 10.-71 | 45 | deletion of segments 72 and 73 |
|  | 10.212 | 10.214 | 43 | deletion of segment 213 |
|  | 10.-118 | 10.-114 | 43 | deletion of segments 115-117 |
|  | 10.164 | 10.156 | 35 | duplication of segments 156-164 |
|  | 10.-200 | 10.-198 | 22 | deletion of segment 199 |
|  | 10.02 | 10.-245 | 21 | inversion |
|  | 10.-03 | 10.-01 | 13 | deletion of segment 2 |
|  | 10.245 | 10.247 | 13 | deletion of segment 246 |
| yMS638 | 10.-17 | 10.1 | 54 | inversion |
|  | 10.16 | 10.-09 | 52 | inversion |
|  | 10.-121 | 10.-119 | 44 | deletion of segment 120 |
| yMS639 | 10.-231 | 10.224 | 78 | inversion |
|  | 10.-17 | 10.-15 | 52 | deletion |
|  | 10.23 | 10.-223 | 40 | inversion |
| yYW186 | 5.51 | 5.42 | 41 | in parental strain |
|  | 5.116 | 5.-112 | 37 | inversion |
|  | 5.-117 | 5.113 | 32 | inversion |
| yYW187 | 10.-97 | 10.82 | 45 | inversion |
|  | 5.51 | 5.42 | 36 | in parental strain |
|  | 10.96 | 10.-81 | 26 | inversion |
| yYW195 | 5.-48 | 5.-46 | 69 | deletion |
|  | 5.12 | 5.07 | 56 | deletion |
|  | 5.51 | 5.42 | 52 | in parental strain |
|  | 5.-45 | 5.-43 | 46 | deletion |
| yYW196 | 5.51 | 5.42 | 59 | in parental strain |

REFERENCES

1. Richardson, S. et al. Design of a synthetic yeast genome. *Science* 355, 1040-1044 (2017).
2. Hoess, R., Wierzbicki, A., & Abremski, K. The role of the loxP spacer region in P1 site-specific recombination. *Nucl. Acid. Res.* 14, 2287-2300 (1986).
3. Dymond, J. et al. Synthetic chromosome arms function in yeast and generate phenotypic diversity by design. *Nature* 477, 471-477 (2011).
4. Cheng, T-H. et al. Controlling gene expression in yeast by inducible site-specific recombination. *Nucl. Acid. Res.* 28, 1-6 (2000).
5. Dymond, J. & Boeke, J. The *Saccharomyces cerevisiae* SCRaMbLE system and genome minimization. *Bioeng. Bugs* 3, 1-4 (2012).
6. Brachmann, C. et al. Designer deletion strains derived from *Saccharomyces cerevisiae* S288C: a useful set of strains and plasmids for PCR-mediated gene disruption and other applications. *Yeast* 14, 115-132 (1998).
7. Wu, Y. et al. Bug mapping and fitness testing of chemically synthesized chromosome X. *Science* 355, eaaf4706 (2017).
8. Xie, Z. et al. "Perfect" designer chromosome V and behavior of a ring derivative. *Science* 355, eaaf4704 (2017).
9. Liti, G. et al. Population genomics of domestic and wild yeasts. *Nature* 458, 337-341 (2009).
10. Cubillos, F. et al. Generation of a large set of genetically tractable haploid and diploid *Saccharomyces* strains. *FEMS Yeast Res.* 9, 1217-1225 (2011).
11. Wanke, V. et al. Caffeine extends yeast lifespan by targeting TORC1. *Mol. Microbio.* 69, 277-285 (2008).
12. Rallis, C., Codlin, S., & Bähler, J. TORC1 signaling inhibition by rapamycin and caffeine affect lifespan, global gene expression, and cell proliferation of fission yeast. *Aging Cell* 12, 563-573 (2013).
13. Gerik, K., Li, X., Pautz, A. & Burgers, P. Characterization of the two small subunits of *Saccharomyces cerevisiae* DNA polymerase delta. *J Biol. Chem.* 273, 19747-19755 (1998).
14. Kapitzky, L. et al. Cross-species chemogenomic profiling reveals evolutionarily conserved drug mode of action. *Mol. Sys. Bio.* 6, 1-13 (2010).
15. Caspeta, L. et al. Altered sterol composition renders yeast thermotolerant. *Science* 346, 75-78 (2014).
16. Reinke, A., Chen, J., Aronova, S., & Powers, T. Caffeine targets TOR complex I and provides evidence for a regulatory link between the FRB and kinase domains of Tor1p. *J. Biol. Chem.* 281, 31616-31626 (2006).
17. Yona, A. et al. Chromosomal duplication is a transient evolutionary solution to stress. *Proc. Nat. Acad. Sci.* 109, 21010-21015 (2012).
18. Beach, R. et al. Aneuploidy causes non-genetic individuality. *Cell* 169, 229-242 (2017).
19. Shen, Y. et al. Deep functional analysis of synII, a 770-kilobase synthetic yeast chromosome. *Science* 355, eaaf4791 (2017).
20. Mitchell, L. et al. Synthesis, debugging, and effects of synthetic chromosome consolidation: synVI and beyond. *Science* 355, eaaf4831 (2017).
21. Zhang, W. et al. Engineering the ribosomal DNA in a megabase synthetic chromosome. *Science* 355, eaaf3981 (2017).
22. Van Solingen, P. and van der Plaat, J B. Fusion of Yeast Spheroplasts. *J. Bacteriol.* 130, 946-947 (1977).
23. Shen, Y. et al. SCRaMbLE generates designed combinatorial stochastic diversity in synthetic chromosomes. *Genome Res.* 26, 36-49 (2016).

While the invention has been described through specific embodiments, routine modifications will be apparent to those skilled in the art and such modifications are intended to be within the scope of the present invention.

What is claimed is:

1. A method for making a diploid yeast having heterozygosity for at least one chromosome, the method comprising:
   i) mating haploid yeast having at least a first modified chromosome comprising a synthetic chromosome capable of recombination-site-mediated evolution (a SCRaMbLE-ready modification) wherein the SCRaMbLE-ready modification comprises introduced site-specific recombinase recognition sites that can be recognized by a recombinase, with a haploid yeast devoid of the SCRaMbLE-ready modification to obtain diploid SCRaMbLE-ready yeast;
   ii) subsequent to the mating, using the recombinase to recombine the first modified chromosome to obtain heterozygous diploid yeast comprising at least one recombined (SCRaMbLEd) chromosome and a homologous non-SCRaMbLEd chromosome, and
   iii) identifying heterozygous diploid yeast that comprise the at least one SCRaMbLEd chromosome and which have a changed phenotype that is different from the phenotype of the diploid SCRaMbLE-ready yeast.

2. The method of claim 1, wherein the changed phenotype comprises a change in growth rate, growth at a temperature at which the SCRaMbLE-ready yeast do not grow, resistance to a chemical compound, production of a product that is not produced by the diploid SCRaMbLE-ready yeast, production of more of a product than is produced by the diploid SCRaMbLE-ready yeast, or a combination thereof.

3. The method of claim 1, wherein the using the recombinase comprises inducing expression of the recombinase, and/or inducing translocation of the recombinase into the nucleus of the diploid SCRaMbLE-ready yeast, such that at least the first modified chromosome is recombined.

4. The method of claim 1, wherein the heterozygous diploid yeast that have the changed phenotype are subjected to a selection pressure prior to selection, and are then identified based at least in part on a changed phenotype that is correlated with being subjected to the selection pressure.

5. The method of claim 4, wherein the selection pressure comprises exposure to an antibiotic, or to a non-antibiotic small drug molecule, or a change in a culture media component, or a change in temperature, or a combination thereof.

6. The method of claim 5 wherein the selection pressure comprises an increased temperature in which the heterozygous diploid yeast are grown.

7. The method of claim 6, wherein the increased temperature comprises a temperature of between 38 and 42 degrees Celsius, inclusive, and wherein the change in the heterozygous diploid yeast that is correlated with the increased temperature comprises survival of the yeast.

8. The method of claim 1, wherein the using the recombinase is performed for not more than 24 hours.

9. The method of claim 8, wherein the using the recombinase is performed for not more than 12 hours.

10. The method of claim 9, wherein the using the recombinase is performed for not more than 6 hours.

11. The method of claim 1, wherein the heterozygous diploid yeast are *S. cerevisiae* or *S. paradoxus*.

12. The method of claim 1 wherein the recombinase recognition sites comprises a loxP site or a loxPsym site.

13. The method of claim 12, wherein the recombinase that recognizes the recombinase recognition site is Cre recombinase or a modified Cre recombinase.

14. The method of claim 13, wherein the modified Cre recombinase comprises a Cre-estrogen binding domain fusion.

15. The method of claim 12, wherein the recombinase recognition site is duplicated in the first modified chromosome, the first modified chromosome thus comprising at least two of the recombinase recognition sites.

* * * * *